Figure 1:
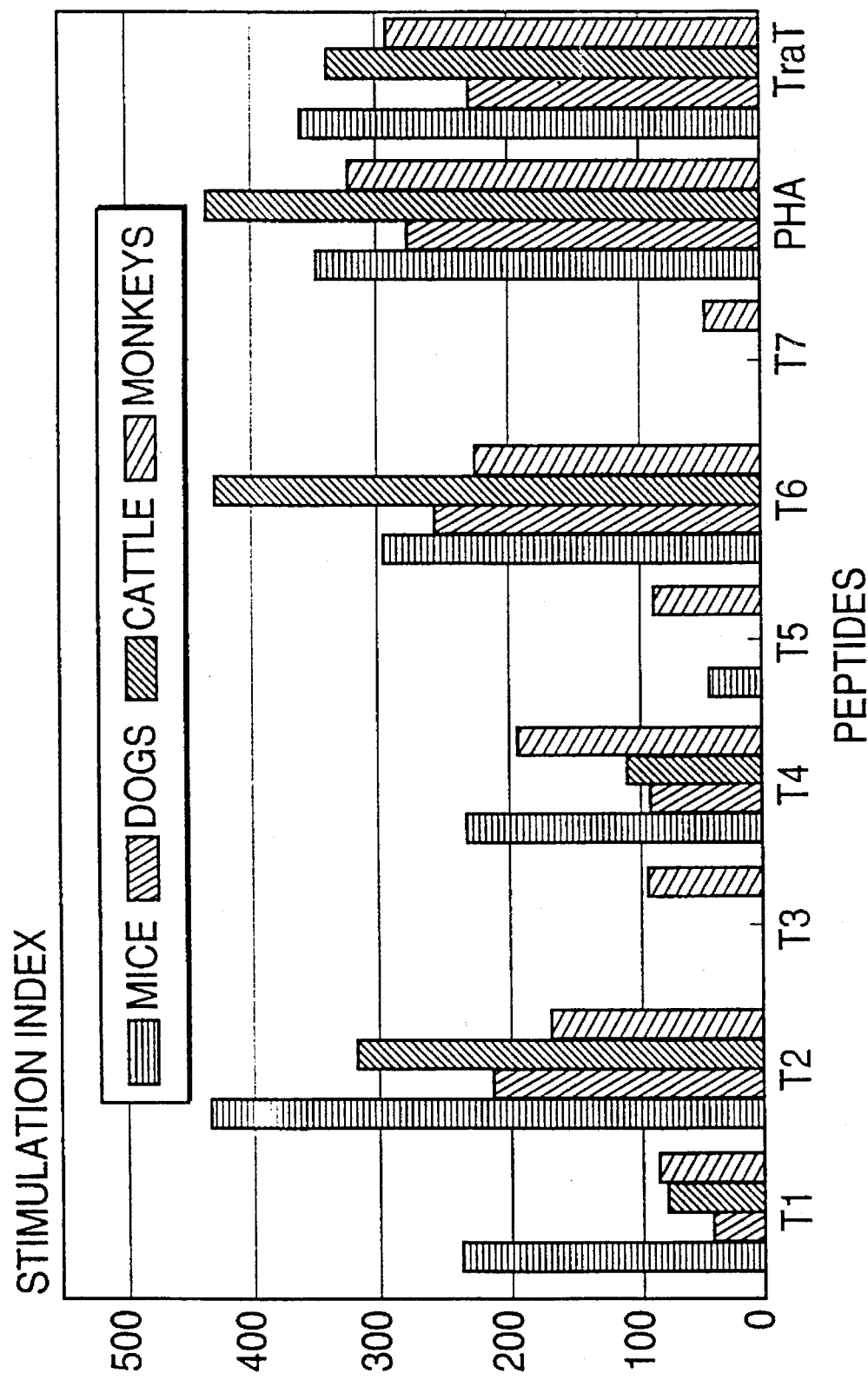

United States Patent [19]
Russell-Jones et al.

[11] Patent Number: 5,500,366
[45] Date of Patent: Mar. 19, 1996

[54] POLYNUCLEOTIDE ENCODING T-CELL EPITOPES OF THE PROTEIN TRAT

[75] Inventors: Gregory J. Russell-Jones, Middle Cove; Andrew F. Geczy, Neutral Bay, both of Australia

[73] Assignee: Biotech Australia Pty. Ltd., Roseville, Australia

[21] Appl. No.: 987,286

[22] PCT Filed: Sep. 17, 1991

[86] PCT No.: PCT/AU91/00429

§ 371 Date: Mar. 16, 1993

§ 102(e) Date: Mar. 16, 1993

[87] PCT Pub. No.: WO92/05192

PCT Pub. Date: Apr. 2, 1992

[30] Foreign Application Priority Data

Sep. 18, 1990 [AU] Australia ................................. PK2361

[51] Int. Cl.$^6$ ........................... C12N 15/31; C12N 15/62; C12N 5/10; A61K 39/08
[52] U.S. Cl. ..................................... 435/252.3; 424/190.1; 424/192.1; 435/69.3; 435/240.2; 435/254.11; 435/320.1; 536/23.4; 536/23.7
[58] Field of Search .............................. 424/190.1, 292.1; 435/69.3, 320.1, 252.3, 254.11, 240.2; 536/23.4, 23.7

[56] References Cited

U.S. PATENT DOCUMENTS 5,403,586  4/1995  Russell-Jones et al. .............. 424/192.1

FOREIGN PATENT DOCUMENTS

| | | |
|---|---|---|
| 35046/89 | 11/1989 | Australia . |
| 87/06590 | 11/1987 | WIPO . |
| 89/06974 | 8/1989 | WIPO . |
| 90/03433 | 4/1990 | WIPO . |

OTHER PUBLICATIONS

Jalajakumari et al. J. Mol. Biol. 198:1–11 1987.
Finlay et al. J. of Bacteriology 166(3): 713–721 (1986).
Adorini, L. et al., "Mechanisms Influencing the Immunodominance of T–cell determinants". *The Journal of Experimental Medicine*, vol. 168; pp. 2091–2104. (Dec. 1988).
Avrameas, S. et al., "Coupling of Enzymes to Antibodies and Antigens", *Scand. J. Immunol.*, vol. 8, (Suppl. 7) pp. 7–23 (1978).
Buus, S. et al., "A Group–specific Inhibitor of Lysosomal Cysteine Proteinases Selectively Inhibits Both Proteolytic Degradation and Presentation of the Dinitrophenyl–poly–L–lysine by Guinea Pig Accessory Cells to T–cells", *The Journal of Immunology*, vol. 136, No. 2, pp. 452–458, (Jan. 1986).
Chanh, T. C. et al., "Synthetic Peptides Homologous to HIV Transmembrane Glycoprotein Suppress Normal Human Lymphocyte Blastogenic Response", *Cellular Immunol.* 111, pp. 77–86 (1988).
Chouaib, S. et al., "Generation of Lymphokine-activated Killer Cells: Synergy Between Tumor Necrosis Factor and Interleukin 2", *Proc. Natl. Acad. Sci. USA* vol. 85, pp. 6875–6879 (Sep. 1988).
Delisi, C. et al., "T–cell Antigenic Sites Tend to be Amphipathic Structures", *Proc. Natl. Acad. Sci. USA*, vol. 82, pp. 7048–7052 (Oct. 1985).
Tsai, C. M. et al., "A Sensitive Silver Stain for Detecting Lipopolysaccharides in Polyacrylamide Gels", *Analytical Biochemistry* 119, pp. 115–119 (1982).
Webster, C. J., "Principles of a Quantitative Assay for Bacterial Endotoxins in Blood that Uses *Limulus* Lysate and a Chromogenic Substrate", *Journal of Clinical Microbiology*, vol. 12, pp. 644–650 (1980).
Bolivar, F. et al., "Construction and Characterization of New Cloning Vehicles, II. A Multipurpose Cloning System", *Gene* 2, pp. 95–113. (1977).
Ogata, R. T. et al., "Nucleotide Sequence Analysis of the Complement Resistance Gene from Plasmid R100", *Journal of Bacteriology*, vol. 151, No. 2, pp. 819–827 (1982).
Perumal, N. B. et al., "The Product of the F Sex Factor traT Surface Exclusion Gene is a Lipoprotein", The Journal of Biological Chemistry, vol. 259, No. 9, pp. 5357–5360 (1984).
Perumal, N. B. et al., "Biochemical Characterization of the F Sex Factor traT surface Gene Product", *Dissertation Abstracts International*, vol. 46, No. 5, p. 160 (1985).
Sukupolvi, S. et al., "Amino Acid Alterations in a Hydrophobic Region of the TraT Portein of R6–5 Increase the Outer Membrane Permeability of Enteric Bacteria", *Mol. Gen. Genet.* 210, pp. 178–180 (1987).
Sukupolvi, S. et al., "Characterization of the TraT Gene and Mutants that Increase Outer Membrane Permeability from the *Salmonella typhimurium* virulence plasmid", *Mol. Microbiol.* 4(1), pp. 49–57 (1990).
Taylor, I. M. et al. "The TraT Lipoprotein as a Vehicle for the Transport of Foreign Antigenic Determinanats to the Cell Surface of *Escherichia coli* K12: Structure–function Relationships in the TraT Protein", Mol. Microbiol. 4(8), pp. 1259–1268 (1990).
Sukupolvi, S. et al., "TraT Lipoprotein, a Plasmid–specified Mediator of Interactions Between Gram–Negative Bacteria and their Environment", Microbiological Reviews, vol. 54, No. 4, pp. 331–334 (1990).
Croft, S. et al., "TraT: A Powerful Carrier Molecule for the Stimulation of Immune Responses to Protein and Peptide Antigens", The Journal of Immunology, vol. 146, No. 3, pp. 793–798 (1991).

*Primary Examiner*—Mary E. Mosher
*Assistant Examiner*—Anthony Caputa
*Attorney, Agent, or Firm*—Foley & Lardner

[57] ABSTRACT

T-cell epitopes of or derived from the TraT protein of *E. coli* have been identified and used in the preparation of complexes with immunogens to enhance or provide immune responses to the immunogens. The complexes can be prepared directly, by chemical linkage, or as fusion proteins. In the latter context, polynucleotides encode a fusion protein which a transformed host can express. The fusion proteins may be expressed intracellularly or exported to and expressed on the surface of the transformant host.

10 Claims, 5 Drawing Sheets

FIG. 5

```
SIGNAL SEQUENCE
ATG AAA AAA TTG ATG ATG GTT GCA CTG AGT TCC ACT CTG GCC CTT TCA GGG TGT GGT GCG ATG AGC ACA GCA   25
Met Lys Lys Leu Met Met Val Ala Leu Ser Ser Thr Leu Ala Leu Ser Gly Cys Gly Ala Met Ser Thr Ala
                                                                      |Gly Ala Met Ser Thr Ala|

ATC AAG AAG CGT AAC CTT GAG GTG AAG ACT CAG GGC AAG ACC ATC TGG CTT GAA CCC GCC AGC GAA CGC       50
Ile Lys Lys Arg Asn Leu Glu Val Lys Thr Gln Gly Lys Thr Ile Trp Leu Glu Pro Ala Ser Glu Arg
|Ile Lys Lys Arg Asn Leu Glu Val Lys|                |Thr Ile Trp Leu Glu|

ACG GTA TTT CTG CAG ATC AAA AAC ACG TCT GAT AAA TCT GAT AAA ATT GCT GAT GCT GTG                    75
Thr Val Phe Leu Gln Ile Lys Asn Thr Ser Asp Lys Ser Asp Lys Ile Ala Asp Ala Val
                                                          T1       |Ile Ala Asp Ala Val|

AAA GCA AAA GGA TAT CAG GTG GTG ACT TCT CCG GAT AAA GCC GAT AAA CAG GCG AAT GTG CTG AAG GCC      100
Lys Ala Lys Gly Tyr Gln Val Val Thr Ser Pro Asp Lys Ala Asp Lys Gln Ala Asn Val Leu Lys Ala
|Lys Ala Lys Gly|                                                               T2

GAT AAG ATG GAT CTG CGG GAG TCT CAG GGA TGG CTG AAC CGT GGT TAT GAA GGC GCA GCA GTT GGT GCA GCG TTA   125
Asp Lys Met Asp Leu Arg Glu Ser Gln Gly Trp Leu Asn Arg Gly Tyr Glu Gly Ala Ala Val Gly Ala Ala Leu
                                                              |Gly Tyr Glu Gly Ala Ala Val Gly Ala Ala Leu|

GGT GCC GGT ATT ACC GGC TAT AAC TCA AAT TCT GCC GGT GTA GGC CTT GCT GGT GTT        150
Gly Ala Gly Ile Thr Gly Tyr Asn Ser Asn Ser Ala Gly Val Gly Leu Ala Gly Leu Val
|Gly Ala Gly Ile Thr|                                         T3       |Gly Leu Ala Gly Leu Val|

GGT ATG GCT GCA GAT GCG ATG GTG GAA GAT GTG GCC CTG CGT CAG ATT GCA GAG CGT ACT     175
Gly Met Ala Ala Asp Ala Met Val Glu Asp Val Ala Leu Arg Gln Ile Ala Glu Arg Thr
                        |Asn Tyr Thr Met Ile|              |Gln Ile Ala Glu Arg Thr|

AAG GCA ACG GTG ACA ACG CAT ACG GAT GTT GCC GCC CTG CGT CAG ACC TCA GGC ACA AAA ATT CAG ACC AGT ACT  200
Lys Ala Thr Val Thr Thr His Thr Asp Val Ala Ala Leu Arg Gln Thr Ser Gly Thr Lys Ile Gln Thr Ser Thr
                      T5                                            |Ser Gly Thr Lys Ile Gln Thr Ser Thr|
                T4

GAA ACA GGT AAC CAG GAC CAT AAA TAC CAG ACC CGT GTT GTT TCA AAT GCG AAC GTT AAC CTG AAA TTT GAA GAG   225
Glu Thr Gly Asn Gln Asp His Lys Tyr Gln Thr Arg Val Val Ser Asn Ala Asn Val Asn Leu Lys Phe Glu Glu
                     T6                                              |Val Asn Leu Lys|

GCG AAG CCT GTT CTC GAA GAC CAA CAG GGT AAC CTG GCC AAA TCA ATC GCA AAT ATT CTC TGA
Ala Lys Pro Val Leu Glu Asp Gln Gln Gly Asn Leu Ala Lys Ser Ile Ala Asn Ile Leu
    T7
```

POLYNUCLEOTIDE ENCODING T-CELL EPITOPES OF THE PROTEIN TRAT

TECHNICAL FIELD

The present invention relates to isolated or synthetic sequences of or derived from TraT (a protein molecule isolated from the outer-membrane of certain strains of *Escherichia coli*) which function as T-cell epitopes. Such sequences can be employed in the preparation of vaccines which involve the use of carrier peptides to enhance antibody production to an immunogen and/or stimulate strong cell-mediated immunity to the immunogen whilst avoiding the use of larger carrier protein molecules.

BACKGROUND ART

The generation of an immune response against a pathogen (bacterial, viral or parasite) depends, in the first instance, on the delivery of the appropriate stimulus to the immune system of the host. The pathogen or infectious agent presents the host with a number of immune-stimulating compounds or antigens which are usually large molecules such as proteins, polysaccharides or glycoproteins. These antigens may provoke one or more different types of reaction from the host in an effort to destroy or eliminate the invading organism. Accordingly, the antigen may stimulate T-cells which provide cell-mediated immunity and/or an antigen may stimulate B cells to initiate the synthesis and secretion of antibody (humoral immunity). The development and maintenance of the individual's protective immune response to a foreign antigen is usually dependent on achieving a critical level of stimulation of both cell-mediated and humoral immunity.

In the generation of a protective immune response, a certain type of T-cell, a helper T-cell is frequently required to assist the B-cell to grow and secrete soluble antibody. These helper T-cells also interact with and recognize antigens on the surface of antigen-presenting cells such as macrophages and, by releasing soluble factors (cytokines), mediate activation and differentiation of B-cells.

Certain small molecules termed haptens, of which short peptides are an example, are usually poorly immunogenic while larger molecules such as proteins and some polysaccharides are usually immunogenic in that they elicit a satisfactory protective response. To obviate the problems of inducing immunity to poorly immunogenic molecules, attempts have been made to enhance their immunogenicity by binding them to "carrier" molecules. These carriers, which are usually immunogenic proteins, function by stimulating the T-cell co-operative effect that occurs with naturally immunogenic molecules. That is to say, a poorly immunogenic antigen, bound to a carrier, will elicit T-cell help in antibody production. By engaging the T-cells with carrier determinants, B-cells will begin antibody production not only to the carrier itself, but also to the bound antigenic determinant.

Although it is widely accepted that the carrier principle is an effective method of improving the efficacy of vaccines, the number of proteins which are ethically accepted for use as potential carrier proteins for human use is relatively limited. These include tetanus toxoid and diphtheria toxoid. The limited number of available carrier proteins means that a large number of vaccine products will employ one of these proteins and multiple immunizations with products conjugated to these carriers increases the possibility that undesirable reactions to these carriers will occur. Also, these carriers have been chosen in the first instance, not for their immunostimulatory characteristics, but rather because they were already registered for human use. It is clear, therefore, that there is a need for an alternative carrier to those currently used in conjugate vaccines which will obviate the immunological problems associated with these vaccines and yet retain the same immunogenicity as the vaccines presently in use or improve on it.

During the past decade it has become clear that certain fragments of proteins, rather than the entire protein molecule, are preferentially recognized by T-cells in association with an appropriate self (Class I or Class II) antigen. These fragments are known as T-cell epitopes and their co-recognition (i.e., in association with certain Class I or Class II molecules) by T-cells ensures the delivery of "T-cell help" so that a B cell can be activated and undergo differentiation to secrete antibody.

It is generally accepted that T-cell recognition of proteins is more complex than antibody binding, and, despite recent advances in our understanding of T-cell epitopes, less clearly understood. However, in the mid 1980s it was suggested that T-cell determinants (epitopes) have a tendency to form stable helical structures in which the hydrophilic groups align on one surface of the helix while hydrophobic residues align on the opposing surface. In this model, it is proposed that the hydrophobic surface would normally be found associated with the MHC antigen while the more hydrophilic surface would be exposed to the T-cell receptor. Accordingly, an algorithm to search a given protein sequence for regions with a tendency to form helical amphipathic structures has been developed and applied to several protein models (De Lisi and Berzofsky, *P N A S* 82: 7048, 1985). In contrast, some workers maintain that T-cell determinants are associated with beta turns within the protein. However, these algorithms frequently fail to detect T-cell epitopes and conversely often select sequences which do not function as T-cell epitopes. In addition, these algorithms can not be used to define the strength or cross-species functionality of selected sequences. A unifying hypothesis of what factors are important for predicting T-cell epitopes has yet to emerge and the identification of such epitopes as well as the determination of their strength is still very much an empirical exercise. Although it is still not clear what a T-cell perceives, there is agreement among several groups using a variety of models that a region of 7–17 amino acid residues in length is required for recognition.

T-cell epitopes from diphtheria toxin, tetanus toxin and cross-reacting material of diphtheria toxin were described in PCT/US89/00388. They differ from the T-cell epitopes of this invention.

Previous work (PCT/AU87/00107) has examined a number of integral membrane proteins for their ability to generate serum antibody responses in the absence of adjuvant. These proteins, which include TraT, have been shown to stimulate high titres of serum antibody in mice, rats, guineapigs and rabbits. The antibody titres elicited by injecting TraT in saline is not significantly increased by the addition of oil-based adjuvants such as Freund's Incomplete Adjuvant (FIA) or MONTANIDE/MARCOL. Covalent attachment of Bovine Serum Albumin or of the dinitrophenyl group or of a peptide antigen to TraT results in a significant enhancement of the immune response to the conjugated material as compared with the response seen when the immunogen is injected without adjuvant or not conjugated to TraT. The antibody response to these conjugates is not significantly increased by the addition of FIA. TraT is a self-adjuvanting carrier molecule which is capable of generating high antibody titres to itself as well as to molecules attached to it.

ABBREVIATIONS

AlOH—aluminium hydroxide
CPM—counts per minute
DEAE—diethylaminoethyl
DMF—dimethyl formamide
DT—diphtheria toxoid
EDTA—ethylene diamine tetraacetic acid
FIA—Freund's incomplete adjuvant
HPLC—High performance liquid chromatography
FCS—Foetal calf serum
LAL assay—Limulus Amoebocyte Lysate Assay
LHRH—Luteinizing hormone releasing hormone
LIP—Liposome
LPS—Lipopolysaccharide
MBS—m-maleimido benzoic acid n-hydroxysuccinimide ester
PBS—Phosphate buffered saline
PHA—Phytohaemagglutinin
PMSF—Phenylmethyl sulphonyl fluoride
QA—Quality assurance
QC—Quality control
RPMI—tissue culture medium
RT—Room temperature
SAP—Saponin
SDS—Sodium dodecyl sulphate
SDS-PAGE—Sodium dodecyl sulphate polyacrylamide gel electrophoresis
TFA—Trifluoroacetic acid
VYDAC—Trade name of chromatography column
ZWIT—ZWITTERGENT

DESCRIPTION OF THE INVENTION

According to the present invention isolated peptide sequences of or derived from TraT that by themselves have unexpectedly high immunostimulatory properties in a range of species have been identified and used. The specific sequences T1, T2, T4 and T6 (SEQUENCE ID Nos 1, 2, 4, and 6 respectively) described herein are recognized by several phylogenetically diverse species, including primates.

To the knowledge of the present inventors, T-cell stimulating peptide sequences that cross several species barriers have not been reported previously.

The finding that TraT (SEQUENCE ID Nos. 16 and 17) was a strong self-adjuvanting carrier molecule led the present inventors to consider that there might be particular peptide sequences within this protein which are preferentially recognized by T-cells. As a result of scanning the TraT molecule and considering factors which might enhance activity as a T-cell epitope, seven peptides derived from the TraT molecule were synthesized and then tested in T-cell proliferative assays using T-cells from a variety of animals that had been immunized with the native TraT molecule in saline. A hierarchical pattern of responsiveness to the peptides was observed in the four animal species studied and in particular four of the peptides (T1,T2, T4, T6: SEQUENCE ID Nos 1, 2, 4 and 6 respectively) showed very strong responses in all four species tested. Because these peptide sequences cross several species barriers it is possible that they are recognized by T-cells both within and across species.

The amino acid sequences of the seven molecules are:

| | |
|---|---|
| T1: | GlyAlaMetSerThrAlaIleLysLysArgAsnLeuGluValLys ThrGlnMetSerGluThrIleTrpLeuGlu (SEQUENCE ID NO. 1) |
| T2: | GlyLeuGlnGlyLysIleAlaAspAlaValLysAlaLysGly (SEQUENCE ID No. 2) |
| T3: | SerGlnTrpLeuAsnArgGlyTyrGluGlyAlaAlaValGlyAla AlaLeuGlyAlaGlyIleThrGly (SEQUENCE ID No. 3) |
| T4: | GlyLeuAlaAlaGlyLeuValGlyMetAlaAlaAspAlaMetVal GluAspValAsn (SEQUENCE ID No. 4) |
| T5: | AspValGlnIleAlaGluArgThrLysAlaThrValThrThrAsp AsnValAlaAlaLeuArgGln (SEQUENCE ID No. 5) |
| T6: | SerThrGluThrGlyAsnGlnHisHisTyrGlnThrArgValVal SerAsnAlaAsnLys (SEQUENCE ID No. 6) |
| T7: | LysValAsnLeuLysThrGluGluAlaLysProValLeuGluAsp GlnLeuAlaLys (SEQUENCE ID No. 7) |

The TraT sequences which correspond to these molecules are shown in FIG. 5 and are as follows:

| | |
|---|---|
| TraT(T1) | GlyAlaMetSerThrAlaIleLysLysArgAsnLeuGluVal LysThrGlnMetSerGluThrIleTrpLeuGlu (SEQUENCE ID No. 1) |
| TraT(T2) | GlyLeuGlnGlyLysIleAlaAspAlaValLysAlaLysGly (SEQUENCE ID No. 2) |
| TraT(T3) | GluSerGlnGlyTrpLeuAsnArgGlyTyrGluGlyAlaAla ValGlyAlaAlaLeuGlyAlaGlyIleThrGly (SEQUENCE ID No. 24) |
| TraT(T4) | GlyLeuAlaAlaGlyLeuValGlyMetAlaAlaAspAlaMet ValGluAspValAsn (SEQUENCE ID No. 4) |
| TraT(T5) | AspValGlnIleAlaGluArgThrLysAlaThrValThrThr AspAsnValAlaAlaLeuArgGln (SEQUENCE ID No. 5) |
| TraT(T6) | SerThrGluThrGlyAsnGlnHisLysTyrGlnThrArgVal ValSerAsnAlaAsnLys (SEQUENCE ID No. 25) |
| TraT(T7) | LysValAsnLeuLysPheGluGluAlaLypProValLeuGlu AspGlnLeuAlaLys (SEQUENCE ID No. 26) |

T1, T2, T4 and T5 are identical to the sequences which appear in the native TraT sequence. T3, T6 and T7 are modified compared with TraT(T3), TraT(T6) and TraT(T7). In T3 the amino terminal 4 residues GluSerGlnGly of TraT(T3) are replaced by SerGln. In T6, the Lys residue from position 9 of TraT(T6) is replaced by His. In T7, the Phe residue from position 6 of TraT(T7) is replaced by Thr. These alterations to the native sequences were made to enhance the T-cell epitope activity of these peptides.

According to a first embodiment of the present invention, there is provided a T-cell epitope comprising a portion of the amino acid sequence of the protein, TraT.

Typically the T-cell epitope is effective across species.

Specific T-cell epitopes according to the present invention include portions of TraT having T-cell epitope activity or derivatives thereof, such as T1, T2, T4 and T6 (SEQUENCE ID Nos 1, 2, 4 and 6) which have sequences as described above. Each of the T-cell epitopes of the invention may be modified. Modifications in accordance with the present invention include the addition of an N-terminal pyroglutamic acid residue, the substitution of an N-terminal glutamic acid residue by a pyroglutamic acid residue and/or the addition or substitiution of a C-terminal cysteinamide as well as the specific modifications made in T3, T6 and T7 and described above. Modified T-cell epitopes of the invention fall within the scope of the present invention and are included within the term "T-cell epitope" when used herein as appropriate, and are included in references to particular T-cell epitopes of the invention as appropriate. In the preparation of fusion proteins of the invention modifications to the epitope to alter internal amino acids or terminal residues may be made posttranslationally or in the coding sequence as appropriate. The modifications should conserve the T-cell epitope activity of the parent molecule.

The invention also provides a complex comprising at least one T-cell epitope of the first embodiment linked to at least one immunogen wherein the immunogen and the epitope are linked such that the at least one T-cell epitope can still function as a T-cell epitope and the at least one immunogen still presents at least one antigenic determinant against which an immune response can be raised.

The invention further provides a vaccine comprising a complex of the invention together with a pharmaceutically acceptable carrier, excipient, diluent and/or adjuvant.

The complexes of the invention may be prepared by a number of routes. They may be prepared directly or by chemical coupling using appropriate linking or coupling agents or by modification of residues to provide sites for linkage. They may also be prepared through recombinant means as fusion proteins.

The at least one "immunogen" which forms part of a complex of the invention is any molecule which it is desirable to use to raise an immune response. Typically, the at least one "immunogen" will be a molecule which is poorly immunogenic, but immunogenic molecules are not excluded. The at least one "immunogen" includes peptides, oligosaccharides, polypeptides, polysaccharides and specific examples include: circumsporozoite surface protein of *Plasmodium falciparum* (CSP); the synthetic immunogen $NH_2$ Cys (Asn Pro Asn Ala)$_4$ (SEQUENCE ID No. 8) derived from CSP; all or part of luteinizing hormone or somatostatin; and immunogenic proteins which are all or part of: the S protein of hepatitis B virus; the AIDS virus; influenza virus; or foot and mouth disease virus; inhibin and FSH.

With regard to the construction of fusion proteins the invention provides a hybrid first polynucleotide molecule which consists of: a polynucleotide sequence which acts as a coding sequence for at least one T-cell epitope of the invention fused to a polynucleotide sequence coding for the amino acid sequence of at least one immunogen.

The hybrid polynucleotide molecule may comprise sequences encoding: at least one isolated T-cell epitope of the invention fused to at least one immunogen; at least one T-cell epitope of the invention inserted within an immunogen; or all or part of the TraT molecule with the at least one immunogen inserted adjacent a T-cell epitope of the invention.

It is recognised that having provided a sequence encoding a particular fusion protein of interest that it would be within the capabilities of a skilled addressee to alter that sequence so that it still encodes a fusion protein having the activity of the parent fusion. One reason such altered fusions can be prepared is because of the degeneracy of the genetic code. Further a skilled addressee would recognise that it is possible to substitute codons for amino acids with similar characteristics at places within a protein without affecting the activity of the molecule as the parent molecule. Further, having identified a desirable fusion or complex it could be modified by inclusion of multimers of the T-cell epitope, and/or the immunogen and/or the introduction of additional T-cell epitopes of the invention. Such altered molecules are also within the scope of this invention.

Preferred hybrid polynucleotide sequences are DNA sequences.

More preferably the sequences of the invention coding for at least one T-cell epitope of the invention are linked to a DNA sequence coding for the amino acid sequence of the at least one immunogen such that the resulting TraT fusion protein is exported to and exposed on the host cell surface.

The invention also provides a fused gene comprising a hybrid DNA sequence of the invention fused to a portable promoter. A preferred promoter according to the invention, is the $P_L$ promoter of the bacteriophage lambda.

Further, the invention provides a recombinant DNA molecule which comprises a DNA sequence of the invention and vector DNA. Typically the vector is plasmid, bacteriophage, viral or cosmid DNA.

A preferred recombinant DNA molecule of the invention includes an expression control sequence operatively linked to the DNA sequence of the invention.

Within the scope of the invention is a process for the manufacture of a recombinant DNA molecule which process comprises the step of: introducing into vector DNA, a DNA sequence of the invention.

The process preferably also includes the step of introducing an expression control sequence into the vector.

The invention also provides a transformant host with the genetic information for the biosynthesis of a complex comprising at least one immunogen and at least one T-cell epitope of the invention such that the resulting fused peptide is exposed on the host cell surface.

However, transformant hosts which only express the fusion intracellularly may also be used with the fusion being purified from the cells in accordance with standard purification procedures.

Suitable hosts include prokaryotic and eukaryotic cells, including: bacteria, for example *E. coli,* Pseudomonas species, Salmonella species and Bacillus species; yeasts and other fungi, for example *Saccharomyces cerevisiae* and Aspergillus species; insect cells, for example cell lines derived from *Spodoptera frugiperda* and *Bombyx mori;* and mammalian cells for example Chinese Hamster ovary cells and other cell lines.

Also included within the scope of the invention is a process for transforming a host, which process comprises the step of: introducing into a host a recombinant DNA molecule according to the invention.

The invention further provides an expression product of a transformant host of the invention, comprising a complex of the invention.

BRIEF DESCRIPTION OF THE DRAWINGS

FIG. 1 shows the T-cell response to T1-T7 (SEQUENCE ID Nos 9–15), PHA and TraT (SEQUENCE ID Nos. 16 and 17) in immunized animals.

FIG. 2 shows the presentation of T1-T7 (SEQUENCE ID Nos 9–15), PHA and TraT (SEQUENCE ID Nos. 16 and 17) by fixed and control macrophages.

FIG. 3 shows T-cell responses to carrier and peptide in monkeys immunized with Pre S2-TraT or PreS2-DT in various formulations.

FIG. 4 shows the structure of p TraT (c), a TraT expression vector. $P_L$=Leftward promoter of Lambda; TT =transcription terminator; Amp$^r$=Ampicillin resistance gene; Region 1302-3597 approximately equals region 2066 (old PvuII site) to 4367 (old EcoRI site) of pBR322; Diagram not to scale.

FIG. 5 SEQUENCE ID Nos. 16 and 17 shows the coding sequence of TraT and the location of TraT (T1–T7). (SEQUENCE ID Nos 1, 2, 24, 4, 5 25 and 26).

BEST MODE FOR CARRYING OUT THE INVENTION

The recombinant DNA techniques, techniques of chemical synthesis, formulation and vaccination used in accordance with this invention are standard techniques known to those skilled in the appropriate arts. For formulating the vaccines of the invention an effective amount of a complex of the invention is formulated with a pharmaceutically acceptable carrier, diluent, excipient and/or adjuvant to provide a vaccine for administration to a host requiring immunisation with the immunogen of interest.

Solid dosage forms suitable for oral administration may include capsules, tablets, pills, powders, and granules. In such solid dosage forms, at least one complex may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may be in the form of pharmaceutically acceptable emulsions, syrups, solutions, suspensions, and elixirs containing inert diluents commonly used in the art such as water. Such compositions may also comprise wetting agents, emulsifying and suspending agents, and sweetening, flavouring, and perfuming agents including sugars such as sucrose, sorbitol, fructose etc, glycols such as polyethylene glycol, propylene glycol etc, oils such as sesame oil, olive oil, soybean oil etc., antiseptics such as alkylparahydroxybenzoate etc, and flavours such as strawberry flavour, peppermint etc.

Suitable excipients, carriers and/or diluents for use in preparation of injectable forms may also be used in preparing injectable vaccines.

Other alternatives would include nasal sprays and other mucosal routes of administration such as suppositories.

The term "pharmaceutically acceptable adjuvant" can mean either the standard compositions which are suitable for human administration or the typical adjuvants employed in animal vaccinations.

At present alum is the only registered adjuvant for human use however, experimental work is being conducted on other adjuvants for human use and it is anticipated that these other adjuvants would be suitable for use in preparing compositions for human vaccination in accordance with this invention.

Suitable adjuvants for the vaccination of animals include but are not limited to saponin, oil emulsions such as Freund's complete or incomplete adjuvant (not suitable for livestock use), MARCOL 52: MONTANIDE 888 (Marcol is a Trademark of Esso. MONTANIDE is a Trademark of SEPPIC, Paris), squalane or squalene, ADJUVANT 65 (containing peanut oil, mannide monooleate and aluminium monostearate), mineral gels such as aluminium hydroxide, aluminium phosphate, calcium phosphate and alum, surfactants such as hexadecylamine, octadecylamine, lysolecithin, dimethyldioctadecylammonium bromide, N,N-dioctadecyl-N',N'-bis(2-hydroxyethyl) propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate. The complexes of the present invention can also be administered following incorporation into liposomes or other micro-carriers, or after conjugation to polysaccharides, proteins or polymers or in combination with QUIL-A to form immunostimulating complexes.

It is recognised that a number of factors will affect the determination of an appropriate dosage for a particular host. Such factors include the age, weight, sex, general health and concurrent disease status of the host. The determination of the appropriate dose level for the particular host is performed by standard pharmaceutical techniques.

The strength of the peptide sequences derived from TraT was evidenced by the demonstration that in squirrel monkeys conjugates of TraT and a peptide HepB-preS2 133–152: SEQUENCE ID No. 18 (where PreS2 represents amino acids 120–145 of the preS2 region of Hepatitis B surface antigen) induced a much stronger T-cell response than conjugates of Diphtheria toxoid (DT) and preS2. DT is an effective carrier protein, with a number of T-cell epitopes, which has been approved for use as a carrier in human vaccines.

EXAMPLE 1

The synthesis of peptides derived from TraT

The seven peptides, T1 to T7 (SEQUENCE ID Nos 1–7), were synthesized on an APPLIED BIOSYSTEMS NO. 430A PEPTIDE SYNTHESIZER with N-terminal pyroGlu and C-terminal Cys-NH$_2$. The peptides were purified by chromatography on G-25 SEPHADEX (PHARMACIA) in 10% Acetic Acid, followed by Reverse Phase HPLC on a VYDAC C-18 column using a linear gradient of 5–60% acetonitrile in 0.1% TFA. The sequences of the peptides synthesised are as follows:

T1: PyroGluGlyAlaMetSerThrAlaIleLysLysArgAsnLeuGluValLysThr GlnMetSerGluThrIleTrpLeuGluCys-NH$_2$ (SEQUENCE ID No. 9)

T2: PyroGluglyLeuGlnGlyLysIleAlaAspAlaValLysAlaLysGlyCys-NH$_2$ (SEQUENCE ID No. 10)

T3: PyroGluSerGlnTrpLeuAsnArgGlyTyrGluGlyAlaAlaValGlyAlaAla LeuGlyAlaGlyIleThrGlyCys-NH$_2$ (SEQUENCE ID No. 11)

T4: PyroGluGlyLeuAlaAlaGlyLeuValGlyMetAlaAlaAspAlaMetValGlu AspValAsnCys-NH$_2$ (SEQUENCE ID No. 12)

T5: PyroGluAspValGlnIleAlaGluArgThrLysAlaThrValThrThrAspAsn ValAlaAlaLeuArgGlnCys-NH$_2$ (SEQUENCE ID No. 13)

T6: PyroGluSerThrGluThrGlyAsnGlnHisHisTyrGlnThrArgValValSer AsnAlaAsnLysCys-NH$_2$ (SEQUENCE ID No. 14)

T7: PyroGluLysValAsnLeuLysThrGluGluAlaLysProValLeuGluAspGln LeuAlaLysCys-NH$_2$ (SEQUENCE ID No. 15)

Purification of TraT

E. coli cells (Strain BTA 1349 containing the plasmid pBTA439, a derivative of plasmid pBR329 into which has been inserted a 6.0 kb EcoR1 fragment of the R100 plasmid which contains the DNA sequence coding for TraT, expressed from the lambda leftward promoter $P_L$), were grown in a fermenter at 30° C. and induced at 42° C. for 2 hours. Following induction, the cells were concentrated and washed with distilled water in an AMICON DC10LA concentrator (0.1 μm hollow fibre cartridge). Cells were removed from the concentrator and the integral membrane proteins extracted from the cells by the addition of a solution containing 0.2M Na Acetate buffer pH 2.5, 2% cetrimide (SIGMA) in 20% ethanol plus 0.2M $CaCl_2$ (final concentration). The extraction was allowed to proceed overnight at room temperature (RT) after which the bacteria were pelleted by centrifugation (17,000 x g, 20 min.).

TraT was precipitated from the supernatant by the addition of ethanol to 50% followed by centrifugation (4000 x g. 10 min). It was then resuspended in 1% ZWITTERGENT, 20 mM Na Acetate buffer, pH 6.5, 20 mM EDTA and further purified by chromatography on DEAE-SEPHAROSE (PHARMACIA) in 20 mM Na Acetate buffer pH 6.5, containing 0.1% ZWITTERGENT (CALBIOCHEM) and 20 mM EDTA. Proteins were eluted using a linear gradient of 0 to 1M NaCl in the loading buffer. Fractions containing the integral membrane proteins were pooled, precipitated with ethanol and resuspended in 10% SDS and further purified by size exclusion chromatography on S-300 SEPHACRYL (PHARMACIA) in 10 mM Tris. HCl pH 8.8 containing 2% SDS, 20 mM EDTA. TraT purified by this method travelled as a single band when analyzed by SDS-PAGE with a molecular weight of 28,000, and was found to be free of LPS when subjected to SDS-PAGE and silver stained by the method of Tsai and Frasch (*Anal. Biochem.* 119: 115, 1982). The TraT protein was found to be contaminated with less than 0.005 ng of LPS/mg of protein when tested in the LAL assay (Webster, *J Clin Microbiol.* 12: 644, 1980).

Immunization of animals and the assessment of T-cell proliferation

Animals were immunized intramuscularly with 50 μg (mice), 200 μg (dogs and monkeys) or 500 μg (cattle) of TraT in saline and boosted 14 to 28 days later with a similar inoculum. Fourteen days after the last injection, peripheral blood lymphocytes (dogs, monkeys and cattle) or lymph node cells (mice) were used as a source of T lymphocytes which were then stimulated in vitro with various concentrations of the peptides [the responses to 50 μg of TraT (SEQUENCE ID Nos. 16 and 17) and 50 μg of T1 to T7 (SEQUENCE ID Nos 9–15, respectively) as well as to 2 μg PHA are given in FIG. 1]. T-lymphocytes were isolated from lymph nodes according to the method of Adorini et al. *J. Exp. Med.* 168: 2091, 1988; while the method of Chouaib et al. (*P. N. A. S.*, 85: 6875, 1988) was followed for the isolation of T-cells from peripheral blood. The method of Adorini et. al. was followed for the assessment of T-cell proliferation. Results are expressed as Stimulation indices, which are calculated by dividing the c.p.m. in the presence of antigen by the c.p.m. in the absence of antigen. Standard errors of the means of triplicate cultures were less than 10% of the Mean.

Results

As can be seen from FIG. 1, significant T-cell responsiveness to 50 μg of T1, T2, T4 and T6 (SEQUENCE ID Nos 9, 10, 12 and 14 respectively) as well as to TraT was seen in all four species, with T2, T4 and T6 (SEQUENCE ID Nos. 10, 12 and 14 respectively) showing particularly strong responses. The high degrees of conservation of the responses to these peptides in a number of species suggests that these peptides may prime for strong antibody responses in a range of phylogenetically diverse species as well as in a range of genetically diverse individuals within a species. T-cell stimulatory peptide sequences that cross several species barriers have not, to our knowledge, been reported in the literature.

Primary and secondary T-cell proliferative responses of human peripheral blood lymphocytes to TraT and to the T-cell epitope peptides The strong in vitro proliferative responses observed to the T-cell peptides (in particular to T2, T4 and T6: SEQUENCE ID Nos 10, 12 and 14 respectively) in the four animal species studied, suggested that a similar hierarchial pattern of responsiveness would also be seen in humans. T-cell epitope peptides which exhibit a permissive association with major histocompatibility complex (MHC) molecules, and are therefore preferentially recognised by T-cells, would be attractive candidates for the production of subunit vaccines because they would be expected to induce an immune response in the majority of individuals in a outbred human population. It was therefore decided to examine T-cell responses in humans to TraT-derived T-cell epitopes.

Because of the logistic problems posed by immunizing humans with TraT (to our knowledge none of the blood donors had been deliberately immunized with TraT), an alternative approach involving in vitro immunization was performed. To test the "universality" of the TraT-derived T-cell stimulatory peptides in humans, heparinized blood samples were obtained from twenty randomly selected donors at a Blood Bank. Peripheral blood lymphocytes (PBL), which are an enriched T-cell population, were stimulated in vitro with TraT or with T1 to T7 (SEQUENCE ID Nos 9–15) in primary cultures, and a portion of the PBL was also restimulated with TraT-pulsed mononuclear cells in secondary cultures. The results in Table 1 show that, in a 3-day primary T-cell proliferation assay, PBL of eight from twenty (40%) donors responded (stimulation index≦3) to at least three (T2, T4, T6: SEQUENCES ID Nos 10, 12 and 14 respectively) of the T-cell peptides as well as TraT (SEQUENCE ID Nos. 16 and 17). However, after a secondary in vitro immunization with TraT-pulsed PBL, responsiveness was observed in the cultures derived from all twenty donors (Table 2) and in addition, a significant boosting effect was seen in cell cultures which responded to primary stimulation. The important implication of this work is that T-cell stimulatory peptides such as T2, T4, T6 (SEQUENCE ID Nos 10, 12 and 14) and possibly T1 (SEQUENCE ID No. 9) could be employed as carriers in subunit vaccines and thereby overcome the unresponsiveness observed in humans as a result of MHC restriction.

TABLE 1

Primary T-cell proliferative responses of human peripheral blood lymphocytes to TraT and the T-cell stimulatory peptides

| DO-NOR | In vitro Stimulants | | | | | | | | |
|---|---|---|---|---|---|---|---|---|---|
| | T1 | T2 | T3 | T4 | T5 | T6 | T7 | TraT | PHA |
| R.E. | 1.0 | 1.2 | 0.7 | 1.1 | 0.7 | 12.8 | 1.2 | 10.3 | 86 |

TABLE 1-continued

Primary T-cell proliferative responses of human peripheral blood lymphocytes to TraT and the T-cell stimulatory peptides

| DO-NOR | T1 | T2 | T3 | T4 | T5 | T6 | T7 | TraT | PHA |
|---|---|---|---|---|---|---|---|---|---|
| A.L. | 15.8 | 22.9 | 1.2 | 15.8 | 2.8 | 31.0 | 0.9 | 42.5 | 56.2 |
| N.M. | 6.4 | 8.0 | 1.8 | 10.7 | 3.0 | 10.3 | 1.7 | 7.8 | 191 |
| S.S. | 0.8 | 0.8 | 0.7 | 0.8 | 3.8 | 0.6 | 0.6 | 3.9 | 133 |
| C.O. | 1.0 | 0.7 | 1.1 | 0.7 | 1.0 | 1.0 | 1.0 | 1.1 | 105 |
| B.G. | 0.9 | 0.9 | 0.8 | 0.8 | 0.7 | 0.8 | 0.8 | 1.0 | 90.6 |
| A.W. | 3.9 | 6.9 | 2.8 | 6.8 | 2.7 | 8.8 | 0.9 | 9.0 | 84.3 |
| B.F. | 0.7 | 1.0 | 1.1 | 1.2 | 1.0 | 4.7 | 1.1 | 4.6 | 141.0 |
| G.F. | 1.0 | 2.0 | 1.2 | 1.4 | 1.5 | 82.8 | 1.9 | 70.8 | 183.0 |
| S.S. | 29.1 | 51.1 | 15.7 | 48.3 | 23.1 | 73.0 | 0.8 | 68.2 | 84.9 |
| D.H. | 28.4 | 43.8 | 8.4 | 52.7 | 25.2 | 65.4 | 0.9 | 70.6 | 97.8 |
| C.B. | 1.1 | 1.1 | 1.3 | 2.1 | 2.5 | 22.2 | 1.1 | 49.2 | 139 |
| G.L. | 1.0 | 0.8 | 1.4 | 1.0 | 1.0 | 1.8 | 1.1 | 1.1 | 357 |
| Z.L. | 0.9 | 0.8 | 0.6 | 1.1 | 1.5 | 0.8 | 0.8 | 0.6 | 217 |
| D.W. | 69.7 | 10.8 | 30.4 | 100.0 | 39.0 | 184.5 | 1.9 | 155.0 | 223 |
| F.W. | 0.8 | 0.7 | 0.7 | 2.0 | 2.0 | 34.6 | 2.8 | 60.5 | 117 |
| K.M. | 0.8 | 31.0 | 17.0 | 37.5 | 18.0 | 47.0 | 0.8 | 41.4 | 51.3 |
| S.M. | 17.3 | 26.7 | 1.0 | 42.7 | 29.5 | 53.4 | 0.8 | 51.5 | 71.0 |
| R.T. | 2.0 | 0.9 | 1.0 | 0.9 | 0.8 | 1.0 | 0.9 | 1.3 | 57.2 |
| J.L. | 1.0 | 0.5 | 0.5 | 0.7 | 0.7 | 0.5 | 0.6 | 0.7 | 57.2 |

Peripheral blood lymphocytes (PBL) were separated from heparinized blood by FICOLL-PAQUE (PHARMACIA) gradient centrifugation. Briefly, 10 ml of blood were layered on 6 ml of FICOLL PAQUE and an enriched T-cell population was separated by centrifugation at 400 g for 40 min. PBL ($10^5$ in 0.2 ml RPMI medium containing 10% human AB serum) were cultured in flat-bottom plates with 50 μg of TraT (SEQUENCE ID Nos. 16 and 17) or one of the T-cell stimulatory peptides (T1 to T7; SEQUENCE ID Nos 9–15) or with 2 μg PHA for 3 days at 37° C. Sixteen hours before harvesting, cells were labelled with 0.5 μCi of tritiated thymidine, harvested and counted in a liquid scintillation counter. Results are expressed as Stimulation Indices which are calculated by dividing the counts per minute (c.p.m.) in the presence of antigen by c.p.m. in the absence of antigen.

TABLE 2

Secondary T-cell proliferative responses of human peripheral blood lymphocytes to TraT and the T-cells stimulatory peptides

| DONOR | T1 | T2 | T3 | T4 | T5 | T6 | T7 | TraT | PHA |
|---|---|---|---|---|---|---|---|---|---|
| R.E. | 6.1 | 10.6 | 4.1 | 12.3 | 3.8 | 17.0 | 1.6 | 15.9 | 227.0 |
| A.L. | 11.8 | 38.0 | 1.8 | 45.0 | 3.6 | 59.0 | 1.8 | 66.0 | 218.0 |
| N.M. | 7.8 | 24.2 | 3.8 | 36.0 | 4.5 | 55.2 | 3.3 | 72.0 | 274.0 |
| S.S. | 1.0 | 11.8 | 5.7 | 12.5 | 0.8 | 14.7 | 1.3 | 16.8 | 379.3 |
| C.O. | 9.2 | 15.8 | 5.9 | 18.3 | 5.3 | 23.2 | 0.6 | 49.2 | 110.5 |
| B.G. | 35.2 | 46.7 | 18.1 | 50.7 | 27.7 | 72.8 | 1.0 | 78.3 | 357.0 |
| A.W. | 2.6 | 25.0 | 5.3 | 42.3 | 6.2 | 55.9 | 2.4 | 66.2 | 317.0 |
| B.F. | 49.8 | 110.0 | 32.0 | 161.0 | 73.0 | 227.0 | 2.2 | 235.0 | 113.0 |
| G.F. | 1.3 | 32.0 | 20.0 | 56.0 | 24.5 | 71.5 | 1.5 | 89.4 | 160.0 |
| S.S. | 23.0 | 51.5 | 14.2 | 69.4 | 40.0 | 110.0 | 8.0 | 133.0 | 309.0 |
| D.H. | 32.3 | 49.0 | 7.7 | 86.0 | 20.8 | 133.0 | 2.5 | 166.6 | 335.0 |
| C.B. | 6.7 | 13.1 | 4.3 | 18.4 | 1.2 | 19.2 | 4.7 | 63.5 | 304.0 |
| G.L. | 2.6 | 41.5 | 1.0 | 28.3 | 2.3 | 22.0 | 5.4 | 17.9 | 206.0 |
| Z.L. | 0.8 | 119.0 | 90.0 | 135.0 | 102.0 | 150.0 | 0.5 | 125.0 | 104.3 |
| D.W. | 56.0 | 150.0 | 28.0 | 185.0 | 26.5 | 216.0 | 2.8 | 236.0 | 116.5 |
| F.W. | 3.2 | 27.5 | 1.9 | 43.0 | 3.8 | 72.0 | 3.9 | 186.0 | 180.2 |
| K.M. | 32.0 | 62.5 | 8.6 | 62.6 | 12.5 | 93.0 | 2.8 | 120.5 | 175.3 |
| S.M. | 8.2 | 32.5 | 2.9 | 66.5 | 15.4 | 92.5 | 2.2 | 146.0 | 218.0 |
| R.T. | 1.2 | 226.0 | 74.6 | 270.0 | 45.7 | 255.0 | 1.0 | 289.0 | 195.0 |
| J.L. | 1.0 | 251.0 | 53.0 | 205.0 | 1.2 | 202.0 | 1.8 | 289.0 | 226.0 |

PBL (6 to $7 \times 10^6$) were pulsed with 50 μg TraT (SEQUENCE ID Nos. 16 and 17) for 30 min at 37° C. and then washed three times with RPMI medium containing 10% human AB serum. The antigen-pulsed cells were set up in 3 ml culture medium in 30-ml culture flasks (COSTAR) and then incubated upright for 8 days at 37° C. A portion of the PBL was set aside and frozen in 10% dimethyl sulphoxide and subsequently used to stimulate the primary cultures. At the end of the primary incubation, the cells were centrifuged at 150 g for 10 min and then stimulated with $2 \times 10^6$ TraT-pulsed frozen and thawed PBL and the restimulated cultures incubated in culture flasks for a further 3 days at 37° C. Viable cells (3 to $4 \times 10^6$) recovered at the end of the secondary culture were washed twice, resuspended at concentration of $10^6$ cells/ml of culture medium and 10% human AB serum. The restimulated PBL ($10^5$ in 0.2 ml Culture Medium) were finally cultured in flat-bottom plates with TraT (SEQUENCE ID No. 16 and 17), T1 to T7 (SEQUENCE ID Nos 9 to 15) or PHA for 3 days as previously described (see legend to Table 1).

T-cell stimulatory peptides from TraT are stronger than those from Diphtheria toxoid (DT)

The in vitro activities of TraT-derived peptides (T1 to T6: SEQUENCE ID Nos 9–14) were compared with those of four peptides reported by others (D1 and D2: SEQUENCE ID Nos 20 and 21; Bixler et al. PCT/US89/00388) or predicted (D3 and D4: SEQUENCE ID Nos 22 and 23) to have strong T-cell stimulatory activity prepared with N and/or C-terminal modification. DT is widely used as a carrier molecule for providing T-cell help for immunogens conjugated to it. For ethical reasons it was not possible to immunise humans with TraT (SEQUENCE ID Nos. 16 and 17). Therefore normal blood donors whose lymphocytes responded to both DT and TraT in vitro were chosen; about 60% of randomly selected blood donors respond to TraT in vitro (see Table 1). The data in the Table 3 below show that in four out of five of those individuals, the responses to the TraT molecule were at least as high as those to DT. Furthermore, the proliferative responses induced by T4 (SEQUENCE ID No. 12) and T6 (SEQUENCE ID NO. 14) in primary cultures were 2- to 3-fold higher than by any of the DT-derived peptides (D1 to D4: SEQUENCE ID Nos 20 to 23). Note that the responses to T6 (SEQUENCE ID No. 14) are almost as strong as those to the TraT molecule itself, suggesting that T6 has an extremely high binding affinity for the MHC. In contrast, the responses to D1 and D4 (SEQUENCE ID Nos 20 and 23) are much lower than to the native DT molecule.

These results show that at least two of the TraT-derived peptides have stronger T-cell stimulatory activity than any of the four selected DT-derived sequences and hence the data indicate the superior utility of these molecules in human vaccine formulations.

TABLE 3

T-cell stimulatory activity of peptides from TraT and Diphtheria toxoid (DT)

| Stimulant | Human Donors | | | | |
|---|---|---|---|---|---|
| (in vitro) | 1 | 2 | 3 | 4 | 5 |
| T1 | 2.4* | 1.8 | 2.3 | 6.2 | 20.4 |
| T2 | 5.6 | 6.6 | 8.2 | 33.2 | 32.0 |
| T3 | 1.2 | 2.0 | 1.8 | 13.0 | 12.7 |
| T4 | 12.8 | 14.2 | 16.6 | 49.3 | 49.5 |

TABLE 3-continued

T-cell stimulatory activity of peptides from
TraT and Diphtheria toxoid (DT)

| Stimulant | Human Donors | | | | |
|---|---|---|---|---|---|
| (in vitro) | 1 | 2 | 3 | 4 | 5 |
| T5 | 3.4 | 2.8 | 3.2 | 7.7 | 26.2 |
| T6 | 16.9 | 18.9 | 22.4 | 56.6 | 45.2 |
| T7 | 2.8 | 2.1 | 3.8 | 14.5 | 18.6 |
| TraT | 20.6 | 24.2 | 28.7 | 64.5 | 48.5 |
| DT | 19.4 | 40.1 | 18.8 | 62.6 | 34.7 |
| D1 | 4.2 | 3.8 | 5.9 | 23.1 | 20.7 |
| D2 | 1.1 | 0.9 | 1.9 | 17.3 | 13.9 |
| D3 | 5.8 | 4.2 | 6.6 | 20.8 | 18.5 |
| D4 | 4.7 | 5.7 | 7.3 | 26.0 | 23.2 |
| PHA | 186.0 | 192.0 | 238.0 | 69.3 | 57.3 |

*Stimulation Index

For details of procedures for assessing T-cell proliferation see the legend to Table 1. T-cells were cultured with 50 μg of TraT, T1 to T7, DT and D1 to D4 or with 2 μg PHA for 3 days at 37° C.

EXAMPLE 2

The Immunogenic Fragment(s) Formed as a Result of "Natural" Processing of TraT Appear to Interact with Major Histocompatability Complex (MHC) Class II Antigens at Least as Effectively as the Peptides T1, T2, T4 and. T6. (SEQUENCE ID Nos 1, 2, 4 and 6)

Immunization of animals and antigen presentation by macrophages

Mice (CBA or C57BL/6J) were immunized subcutaneously with 50 μg TraT (SEQUENCE ID Nos. 16 and 17) in saline and 10 days after priming, the animals were injected intraperitoneally with 1 ml MARCOL oil to induce a peritoneal exudate (PE). Three days later, the mice were sacrificed, the PE harvested and the macrophages separated as described by Buus and Werdelin (J. Immunol. 136: 452, 1986). Macrophages were fixed with paraformaldehyde, essentially as described by Buus and Werdelin (see above). Briefly, macrophages ($5\times10^6$) were treated with 1% paraformaldehyde in 0.1M PBS for 2 min. and the reaction was stopped by the addition of 0.15M glycine-PBS buffer. The fixed macrophages were washed three times in buffer, suspended in RPMI (10% FCS) and $10^5$ cells pulsed with TraT (SEQUENCE ID Nos. 16 and 17) (50 μg), PHA (2 μg) or with the peptides, T1 to T7 (SEQUENCE ID Nos 9–15) (50 μg) for 30 min. at 37° C.; unfixed or control macrophages were also pulsed with antigen for 30 min. at 37° C. After three washes to remove excess antigen, $10^5$ antigen-pulsed paraformaldehyde-fixed or untreated macrophages were combined with $10^5$ TraT-immune T lymphocytes (prepared as described in EXAMPLE 1) and the cells incubated for 72 h at 37° C. Stimulation was determined as described in the previous section.

Results

Figure 2:
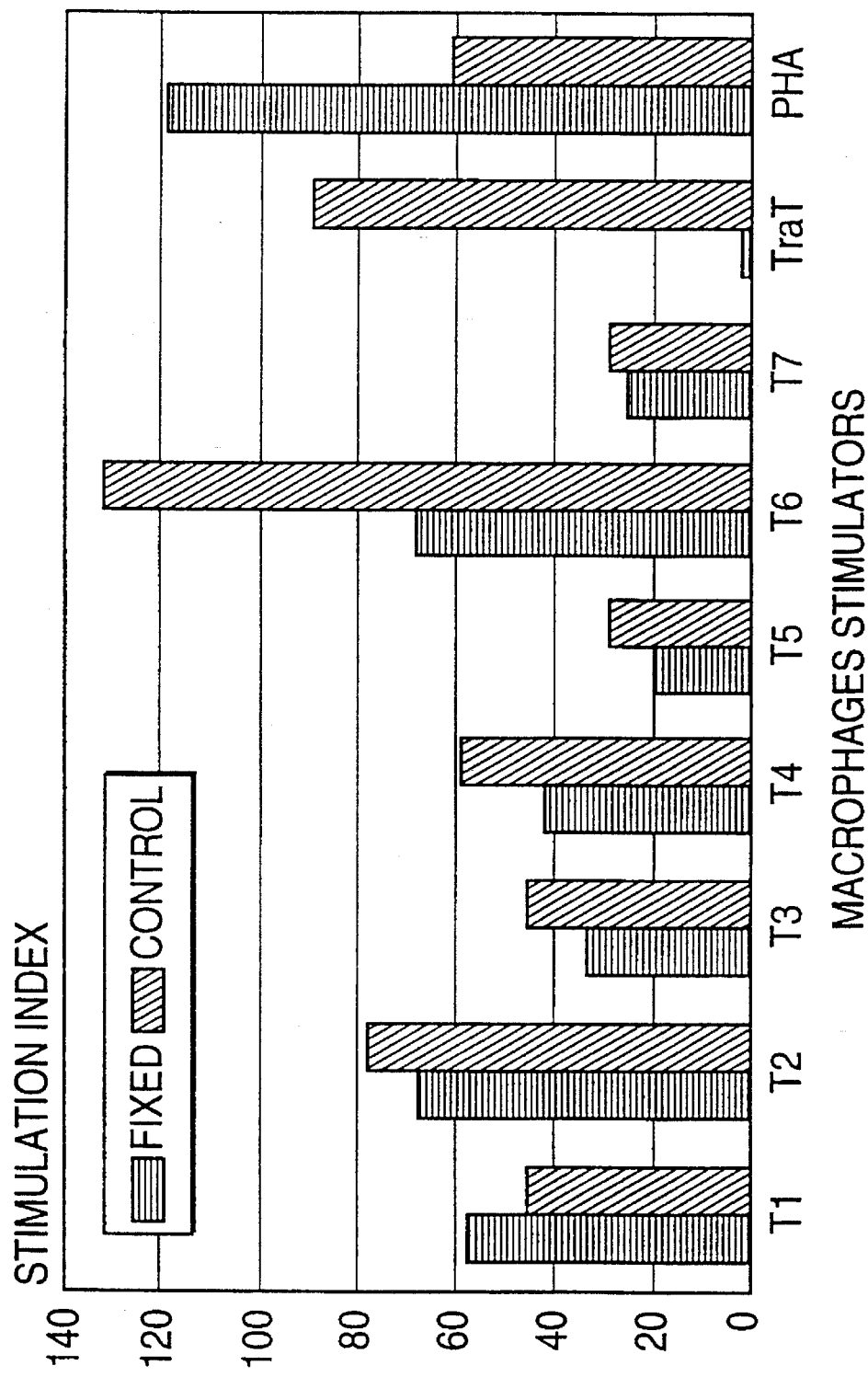

As shown in FIG. 2, fixed macrophages were almost as efficient as untreated macrophages in presenting the four peptides T1, T2, T4 and T6 (SEQUENCE ID Nos 9, 10, 12 and 14) to T lymphocytes, although T6 (SEQUENCE ID No 14) appears to require more processing than the other three peptides. By contrast, fixed macrophages were unable to present the native TraT molecule, presumably because TraT needs to be processed by viable macrophages before it is recognized by T-cells. The data therefore, suggest that the fragments which result from natural processing of TraT, must be very similar to the TraT derived peptides in terms of their interaction with Class II molecules on the surface of the macrophage. If the peptide fragments derived from TraT were vastly different from the naturally processed fragments they would not without further processing interact with macrophages to stimulate T-cells. It is of interest that these Class II molecules appear to remain intact despite the paraformaldehyde treatment. These observations further suggest that the four peptides, T1, T2, T4 and T6 (SEQUENCE ID Nos 1, 2, 4 and 6), may indeed play an important role in the generation of antibody responses in vivo.

EXAMPLE 3

In Squirrel Monkeys, PreS2-TraT Conjugates Induce Stronger T-cell Responses than PreS2-Conjugates of Diphtheria Toxoid (DT)

Synthesis of peptide and its conjugation to the Carrier

A peptide containing part of the highly immunogenic preS2 peptide (amino acids 120–145 of the preS2 region of Hepatitis B) plus some further sequence consisting of amino acids 133–152 viz. Asp-Pro-Arg-Val-Arg-Gly-Leu-Tyr-Phe-Pro-Ala-Gly-Gly-Ser-Ser-Ser-Gly-Thr-Val-Cys: SEQUENCE ID No. 18) was synthesized on an APPLIED BIOSYSTEMS No. 430A PEPTIDE SYNTHESIZER. The peptide was purified by chromatography on G-25 SEPHADEX (PHARMACIA) in 10% Acetic Acid, followed by Reverse Phase HPLC on a VYDAC C-18 column using a linear gradient of 5–60% acetonitrile in 0.1% TFA.

Diphtheria toxoid (DT); (Commonwealth Serum Laboratories, Melbourne, Australia, 1570 Lf units/ml) was precipitated in 80% ethanol and resuspended in 0.1M Phosphate buffer, pH7.0. It was then activated with a 60-fold molar excess of m-maleimido benzoic acid n-hydroxysuccinimide ester (MBS, SIGMA Chemical Co; made up at 10 mg/ml in DMF) for 30 min. at 22° C. The activated DT was precipitated with 80% ethanol, resuspended in 0.1M Phosphate buffer, pH7.0 and mixed with a 20-fold molar excess of preS2 peptide for 3 hr. at 22° C. The conjugate was dialysed overnight against PBS.

TraT was precipitated in 50% ethanol, resuspended in 50 mM Phosphate buffer, pH 7.0 containing 1% ZWITTERGENT and activated with 10-fold of MBS for 30 min. at 22° C. The activated TraT was mixed with a 14-fold molar excess of preS2 (SEQUENCE ID No. 18) peptide for 3 hr. at 22° C. The conjugate was then dialysed overnight against PBS containing 0.1% ZWITTERGENT. The average number of preS2 groups (based on amino acid analysis) per molecule of protein carrier were 2 (TraT) and 10 (DT) respectively.

Formulations

ALHYDROGEL: PreS2-TraT or PreS2-DT (2.5 mg in 0.5 ml) was added to 0.5 ml of ALHYDROGEL and made up to 2.5 ml with PBS and ZWITTERGENT (0.5%).

Saponin: PreS2-TraT or PreS2-DT (2.5 mg in 0.5 ml) was added to 2.5 mg Saponin and then made up to 2.5 ml with PBS.

ZWITTERGENT: TraT- or DT- conjugates (2 mg in 0.5 ml) were made up to 2 ml with PBS and ZWITTERGENT (0.5%).

Liposomes: (A) TraT- or DT- conjugates, following precipitation with 80% ethanol, were resuspended in 1 ml of 10% octylglucoside in 10 mM Hepes. (B) 1 ml of chloroform containing phosphatidyl ethanolamine (16 mg) and phosphatidylcholine (4 mg) were placed in a flask and the chloroform evaporated off under vacuum. 1 ml of the octylglucoside solution (A) was added to (B) and the formulation solubilized by sonication, followed by overnight dialysis against PBS.

Squirrel monkeys were immunized intramuscularly on days 0 and 42 with 200 µg of each of the conjugates (preS2-TraT or preS2-DT) in the various formulations (zwit=ZWITTERGENT; AlOH=ALHYDROGEL; Sap=Saponin; Lip=Liposomes). Peripheral blood lymphocytes taken at day 56 were used as a source of T-cells which were then stimulated in vitro with various concentrations of TraT, DT or preS2 as described in EXAMPLE 1. Results (Proliferative responses to 50 µg of TraT, DT or preS2) are expressed as Stimulation indices. Standard errors of the means of triplicate cultures were less than 10% of the Mean.

Results

Figure 3:
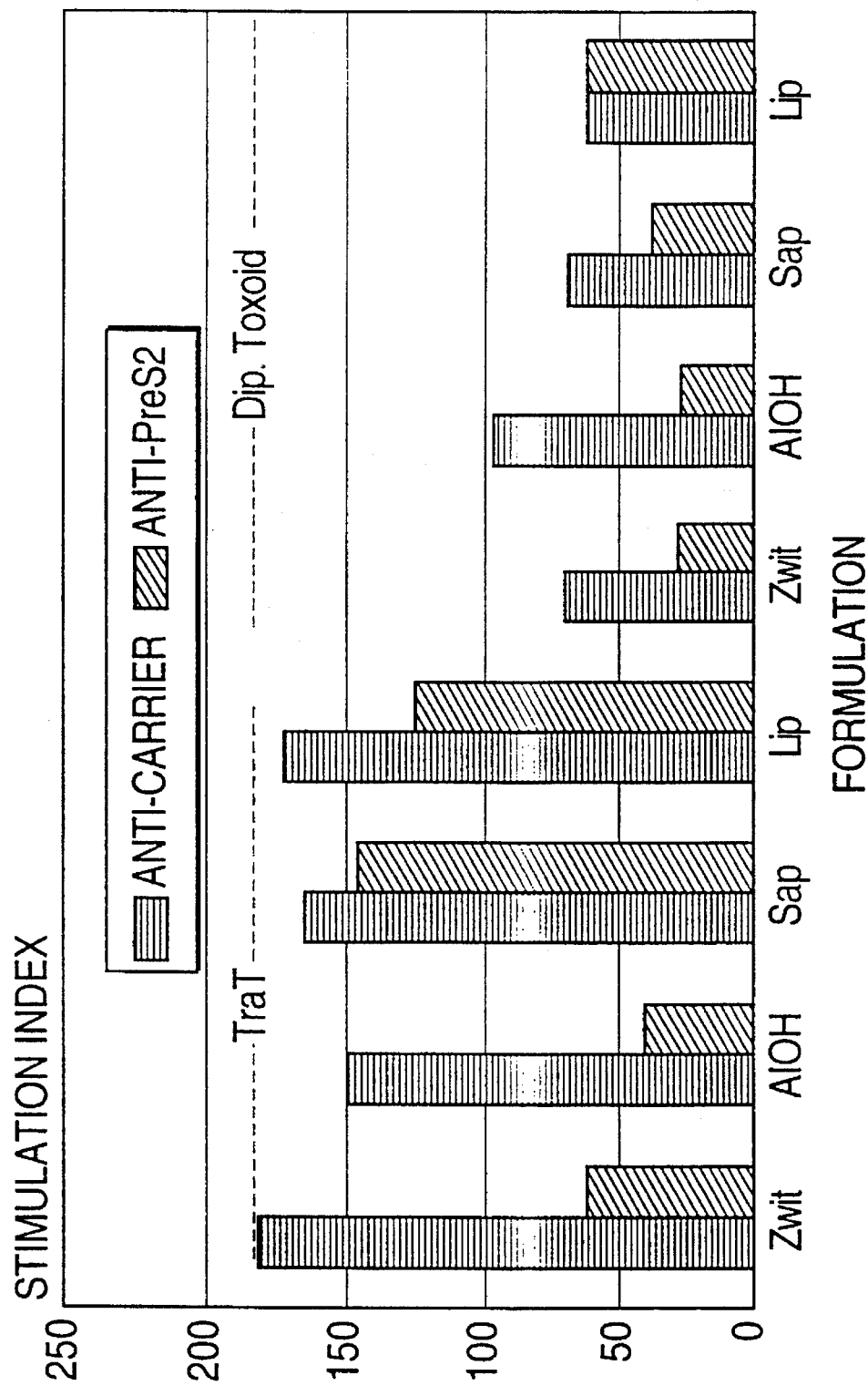
Figure 4:

The results in FIG. 3 show that T-cell proliferative responses to TraT were 2- to 3-fold higher than to Diphtheria toxoid. Furthermore, the anti-PreS2 responses in PreS2-TraT-immunized monkeys were 3- to 4-fold higher than in PreS2-Diphtheria toxoid-immunized animals. The superior T-cell responses generated in response to TraT suggests that this protein (or one of its T-cell stimulatory sequences) may be a useful component of vaccines especially those against viral and parasitic diseases. There is impressive evidence that for many viral and parasitic infections, effector T-cells are primarily responsible for clearance of the infection.

EXAMPLE 4

Peptide Sequences (T2, T4, T6: SEQUENCE ID Nos 2, 4 and 6) Derived from TraT Prime for Strong Antibody Responses to a Peptide Attached to Them After we had identified and documented the existence of strong T-cell stimulatory peptide sequences within TraT, it was necessary to determine whether the delineated regions of TraT could function as effective carrier molecules. The peptide gp120 (amino acids 254–274 of the conserved domain of the gp120 region of HIV1) was used to provide an antigenic determinant. The ability of T-cell stimulatory sequences to deliver T-cell help and therefore prime for antibody responses to peptides attached to them, is an important feature of T-cell epitope peptides. Accordingly, mice were immunized with glutaraldehyde conjugates of each of the seven peptides T1 to T7 (SEQUENCE ID Nos 9–15) and the gp 120 peptide, emulsified in MONTANIDE/ MARCOL (9:1) adjuvant, and boosted 21 days after the primary immunization. The antibody responses elicited in these animals are depicted in Table 4. These results show that the peptides (T2, T4 and T6: SEQUENCE ID Nos 10, 12 and 14) that elicited strong T-cell responses also primed for the highest antibody responses to the peptide gp120 demonstrating their utility as carriers. Because these peptides have strong T-cell stimulatory activity, poor to negligible antibody levels were seen in response to the strong peptides (T2, T4 and T6: SEQUENCE ID Nos 10, 12 and 14) themselves.

Preparation of Glutaraldehyde conjugates of gp120 peptide and the T-Cell epitope peptides The two-step glutaraldehyde procedure of Avrameus et al. (Scand. J. Immunol. 8: 7, 1978) was followed. Briefly, the gp120 peptide (1 mg/ml) in 0.1M PBS pH 6.8 was reacted with 0.2% glutaraldehyde for 2 hr. at 22° C. Following overnight dialysis against 0.1M carbonate/bicarbonate buffer pH 9.5, the glutaraldehyde activated gp 120 was added to the various peptides (T1 to T7: SEQUENCE ID Nos 9–15) at a molar rate of 1:1 and reacted for 24 hr at 22° C. The conjugates were suspended in 1 ml of PBS and emulsified in MONTANIDE/MARCOL (9:1).

Groups of five female C57BL/6J mice (20–25 g) were immunized subcutaneously on days 0 and 21 with 100 µg of glutaraldehyde conjugates of each of the peptides (T1 to T7: SEQUENCE ID Nos 9–15) and the gp 120 peptide, emulsified in MONTANIDE/MARCOL (9:1) or with the gp120 peptide in saline. Animals were bled at 14 days after the second injection and anti-carrier (T1 to T7: SEQUENCE ID NOS. 9–15) and anti-peptide (gp120) responses were estimated by a standard ELISA using plates coated with the T1 to T7 (SEQUENCE ID Nos 9–15) peptides or with gp120.

Results

The results in Table 4 show that the T-cell stimulatory peptides T2, T4, T6 (SEQUENCE ID Nos 10, 12 and 14) and possibly T1 (SEQUENCE ID No. 9) primed for the highest antibody responses to the peptide (gp 120) attached to them. As anticipated, weak to negligible antibody titres were seen in response to these peptides (T1, T2, T4 and T6: SEQUENCE ID Nos 9, 10, 12 and 14). Because they are T-cell epitopes they are unlikely to stimulate B cells well. By contrast, virtually no response was seen in animals immunized with gp120 in saline. Therefore these T-cell stimulatory peptides will be useful for priming antibody responses to peptide antigens. Such antigens of commercial utility may include but are not limited to luteinising hormone, somatostatin, inhibin, FSH, foot and mouth disease peptide, Hepatitis B pre S2 peptide, malaria peptides, Herpes or influenza peptides.

TABLE 4

Anti-Carrier and Anti-Peptide responses in mice immunized with gp 120 -T-cell stimulatory peptide conjucates.
ANTIBODY RESPONSE

| Immunization Groups | Anti-Carrier | Anti-gp-120 peptide |
|---|---|---|
| Saline | 1 | 1 |
| gp 120-T1 | 2 | 838 |
| gp 120-T2 | 1 | 2,612 |
| gp 120-T3 | 1,234 | 52 |
| gp 120-T4 | 1 | 3,110 |
| gp 120-T5 | 2 | 158 |
| gp 120-T6 | 3 | 3,431 |
| gp 120-T7 | 400 | 13 |
| gp 120 | 1 | 13 |

Antibody titres are expressed as the arithmetic mean of the reciprocal of the antiserum dilution which gave an ELISA reading of 0.5 after 45 min. at 25° C.

The strong T-cell stimulation observed with these peptides that prime for B-cell responses to the attached immunogen could also be achieved by the incorporation of the T-cell epitope sequences into fusion proteins specifically designed for the presentation of peptide antigens.

Immunogenic fusion proteins comprising the T-cell epitopes and protein or peptide antigens can be produced from a recombinant gene encoding the fusion protein when expressed in an appropriate host-vector system. These chimaeric proteins may take various forms. The antigen may be located adjacent to the T-cell epitope such as T2 (SEQUENCE ID No 2) or T6-(SEQUENCE ID No. 25) with TraT essentially intact (for example, luteinising hormone releasing hormone [LHRH]/TraT fusions); the T-cell epitopes alone may be inserted within the protein antigen. For example T2 (SEQUENCE ID No. 2) or T6 (SEQUENCE ID No. 6 or 25) may be inserted into the tick antigen BM86 (described as WGL+ in PCT/AU87/00401); or parts of TraT bearing T2 (SEQUENCE ID No. 2) and/or T6 (SEQUENCE ID No. 25) may be located close to antigenic portions of a protein (for example, T2,T6/TraT and luteinising hormone).

A suitable source of DNA encoding the T-cell epitopes of the invention is ATCC 67331.

EXAMPLE 5

Improvement of vaccine efficacy by the use of strong universal T-cell epitopes One of the major drawbacks to the development of effective vaccines to diseases such as AIDS, has been the presence in otherwise immunogenic molecules, such as gp120 (an immunodominant external envelope protein of HIV) of "suppressor regions" which interfere with the development of effective immune responses to these proteins. In order to elicit protective immune responses to these proteins it is proposed to remove these sequences and to replace them with more immunogenic sequences.

T-cell epitope sequences derived from TraT possess unexpectedly high immuno-stimulatory properties in a range of phylogenetically diverse species. These diverse T-cell epitope peptides which manifest a permissive association with major histocompatibility complex (MHC) molecules, and are therefore preferentially recognized by T-cells, would be expected to elicit strong T-cell immunity in the majority of individuals in an outbred population.

Two suppressor regions, corresponding to amino acid sequences 735–752 and 846–860 of the transmembrane glycoprotein of HIV, have been shown to exert a marked inhibition of the human blastogenic responses to mitogens and alloantigens (Chanh, T. C., Kennedy, R. C. and Kanda, K. *Cell Immunol.* 111: 77–86. 1988).

Using recombinant DNA technology, the "suppressor regions" in a number of prospective vaccine proteins including gp 120 are removed and replaced with immunostimulatory peptides derived from TraT. This approach results in vaccines which elicit strong protective immunity in hosts from a broad spectrum of MHC backgrounds. In the first instance the removal of suppressor regions will improve the immunogenicity of the molecule and the replacement of suppressor regions with immunostimulatory regions will further increase the immunogenicity of the modified molecule. The replacement of the suppressor region(s) with a strongly T-cell stimulatory region such as T6, will increase the immunogenicity of the modified recombinant molecule. This molecule would substitute for the native gp120 molecule where this modified molecule is used as a basis of a vaccine e.g. a sub-unit vaccine or as part of inactivated viral particles.

For example, the suppressor region of HIV corresponding to the amino acid sequence (735–752):

Tyr-Asp-Arg-Pro-Glu-Gly-Ile-Glu-Glu-Glu-Gly-Gly (735)

Glu-Arg-Asp-Arg-Asp-Arg-Ser-Gly-Cys (SEQUENCE ID No. 19) (752)

is replaced by the- TraT-derived T6 peptide:

Ser-Thr-Glu-Thr-Gly-Asn-Gln-His-His-Tyr-Gln-Thr-Arg-Val-Val-Ser-Asn-Ala-Asn-Lys (SEQUENCE ID No. 6)

Industrial Application

The current invention is of value in the preparation of vaccines for use in animals and humans. The use of T-cell epitope peptides as carrier molecules will enhance antibody production as well as stimulate cell-mediated immunity while avoiding many of the disadvantages of using larger protein carrier molecules.

Deposition of Strains

BTA 1349 was deposited in accordance with the provisions of the Budapest Treaty with the American Type Culture Collection of 12301 Parklawn Drive, Rockville Md. 20852 U.S.A. on 2 Mar. 1987 under accession number ATCC 67331.

References

Adorini et al (1988) J Exp. Med. 168 2091
Avraemeus et al (1978) Scand. J. Immunol. 8 7
Bolivar et al (1977) Gene 2 95
Chanh, et al (1988) Cell Immunol. 111: 77–86
Chouaib et al (1988) PNAS 85 6875
De Lisi and Berzofsky (1985) PNAS 82 7048
Ogata et al (1982) J. Bacteriol 151 819
Perumal and Minkley (1984) J. Biol. Chem 259 5359
Tsai and Frasch (1982) Anal. Biochem. 119 115
Webster (1980) J. Clin. Microbiol. 12 644
Buus and Werdelin (1986) J. Immunol. 136 452
PCT/US89/00388
PCT/AU87/00107

---

We claim:

1. A polynucleotide molecule consisting of a nucleotide sequence encoding an amino acid sequence selected from the group consisting of:
   (a) Gly Ala Met Ser Thr Ala Ile Lys Lys Arg Asn Leu Glu Val Lys Thr Gln Met Ser Glu Thr Ile Trp Leu Glu (SEQ ID NO: 1);
   (b) Gly Leu Gln Gly Lys Ile Ala Asp Ala Val Lys Ala Lys Gly (SEQ ID NO:2);
   (c) Gly Leu Ala Ala Gly Leu Val Gly Met Ala Ala Asp Ala Met Val Glu Asp Val Asn (SEQ ID NO:4);
   (d) Ser Thr Glu Thr Gly Asn Gln His His Tyr Gln Thr Arg Val Val Ser Asn Ala Asn Lys (SEQ ID NO:6); and
   (e) Ser Thr Glu Thr Gly Asn Gln His Lys Tyr Gln Thr Arg Val Val Ser Asn Ala Asn Lys (SEQ ID NO:25),
wherein said amino acid sequence is a T cell epitope.

2. A hybrid polynucleotide molecule encoding a fusion protein, which comprises at least one polynucleotide molecule of claim 1 fused to a second polynucleotide molecule, wherein said second polynucleotide molecule encodes at least one immunogen, and wherein said hybrid polynucleotide molecule does not encode the entire TraT protein.

3. A hybrid polynucleotide molecule encoding a fusion protein, which comprises a first polynucleotide encoding at least one immunogen, into which is inserted at least one polynucleotide molecule of claim 1, wherein said hybrid polynucleotide molecule does not encode the entire TraT protein.

4. The hybrid polynucleotide molecule as in claim 2 or claim 3, wherein said hybrid polynucleotide molecule is a DNA molecule.

5. The DNA molecule of claim 4, wherein said DNA molecule encodes a fusion protein which is exported to and exposed on the surface of a cell that expresses said fusion protein.

6. The DNA molecule of claim 5, wherein said DNA molecule further comprises the PL promoter of bacteriophage lambda.

7. A vector comprising the DNA molecule of claim 5.

8. The vector of claim 7, further comprising an expression control sequence that is operatively linked to said DNA molecule encoding said fusion protein.

9. A transformant host cell, comprising a vector that comprises the DNA molecule of claim 4, wherein said fusion protein contains at least one T cell epitope and at least one antigenic determinant of said immunogen.

10. The transformant host cell of claim 9, wherein said fusion protein is expressed on the cell surface of said transformant host cell.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Gly Ala Met Ser Thr Ala Ile Lys Lys Arg Asn Leu Glu Val Lys Thr
 1               5                  10                  15
Gln Met Ser Glu Thr Ile Trp Leu Glu
            20                  25
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Gly Leu Gln Gly Lys Ile Ala Asp Ala Val Lys Ala Lys Gly
 1               5                  10
```

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Ser Gln Trp Leu Asn Arg Gly Tyr Glu Gly Ala Ala Val Gly Ala Ala
 1               5                  10                  15
Leu Gly Ala Gly Ile Thr Gly
            20
```

( 2 ) INFORMATION FOR SEQ ID NO:4:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Gly Leu Ala Ala Gly Leu Val Gly Met Ala Ala Asp Ala Met Val Glu
 1               5                  10                  15
Asp Val Asn
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Asp  Val  Gln  Ile  Ala  Glu  Arg  Thr  Lys  Ala  Thr  Val  Thr  Thr  Asp  Asn
1                 5                      10                       15

Val  Ala  Ala  Leu  Arg  Gln
                20
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ser  Thr  Glu  Thr  Gly  Asn  Gln  His  His  Tyr  Gln  Thr  Arg  Val  Val  Ser
1                 5                      10                       15

Asn  Ala  Asn  Lys
                20
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Lys  Val  Asn  Leu  Lys  Thr  Glu  Glu  Ala  Lys  Pro  Val  Leu  Glu  Asp  Gln
1                 5                      10                       15

Leu  Ala  Lys
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Cys  Asn  Pro  Asn  Ala  Asn  Pro  Asn  Ala  Asn  Pro  Asn  Ala  Asn  Pro  Asn
1                 5                      10                       15

Ala
```

( 2 ) INFORMATION FOR SEQ ID NO:9:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="RESIDUE 1 IS PYROGLUTAMIC
            ACID"

( i x ) FEATURE:
        ( A ) NAME/KEY: Modified-site
        ( B ) LOCATION: 27
        ( D ) OTHER INFORMATION: /note="RESIDUE 27 IS CYSTEINAMIDE"

( x i ) SEQUENCE DESCRIPTION: SEQ ID NO:9:

```
    Xaa  Gly  Ala  Met  Ser  Thr  Ala  Ile  Lys  Lys  Arg  Asn  Leu  Glu  Val  Lys
    1                   5                        10                       15

Thr  Gln  Met  Ser  Glu  Thr  Ile  Trp  Leu  Glu  Xaa
                   20                  25
```

( 2 ) INFORMATION FOR SEQ ID NO:10:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note="RESIDUE 1 IS PYROGLUTAMIC
            ACID"

( i x ) FEATURE:
      ( A ) NAME/KEY: Modified-site
      ( B ) LOCATION: 16
      ( D ) OTHER INFORMATION: /note="RESIDUE 16 IS CYSTEINAMIDE"

( x i ) SEQUENCE DESCRIPTION: SEQ ID NO:10:

```
    Xaa  Gly  Leu  Gln  Gly  Lys  Ile  Ala  Asp  Ala  Val  Lys  Ala  Lys  Gly  Xaa
    1                   5                        10                       15
```

( 2 ) INFORMATION FOR SEQ ID NO:11:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note="RESIDUE 1 IS PYROGLUTAMIC
            ACID"

( i x ) FEATURE:
      ( A ) NAME/KEY: Modified-site
      ( B ) LOCATION: 25
      ( D ) OTHER INFORMATION: /note="RESIDUE 25 IS CYSTEINAMIDE"

( x i ) SEQUENCE DESCRIPTION: SEQ ID NO:11:

```
    Xaa  Ser  Gln  Trp  Leu  Asn  Arg  Gly  Tyr  Glu  Gly  Ala  Ala  Val  Gly  Ala
    1                   5                        10                       15

Ala  Leu  Gly  Ala  Gly  Ile  Thr  Gly  Xaa
                   20                  25
```

( 2 ) INFORMATION FOR SEQ ID NO:12:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note="RESIDUE 1 IS PYROGLUTAMIC
            ACID"

( i x ) FEATURE:
      ( A ) NAME/KEY: Modified-site (B) LOCATION: 21
(D) OTHER INFORMATION: /note="RESIDUE 21 IS CYSTEINAMIDE"

(xi) SEQUENCE DESCRIPTION: SEQ ID NO:12:

Xaa Gly Leu Ala Ala Gly Leu Val Gly Met Ala Ala Asp Ala Met Val
1               5                   10                  15

Glu Asp Val Asn Xaa
            20

(2) INFORMATION FOR SEQ ID NO:13:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="RESIDUE 1 IS PYROGLUTAMIC
        ACID"

(ix) FEATURE:
    (A) NAME/KEY: Modified-site
    (B) LOCATION: 24
    (D) OTHER INFORMATION: /note="RESIDUE 24 IS CYSTEINAMIDE"

(xi) SEQUENCE DESCRIPTION: SEQ ID NO:13:

Xaa Asp Val Gln Ile Ala Glu Arg Thr Lys Ala Thr Val Thr Thr Asp
1               5                   10                  15

Asn Val Ala Ala Leu Arg Gln Xaa
            20

(2) INFORMATION FOR SEQ ID NO:14:

(i) SEQUENCE CHARACTERISTICS:
    (A) LENGTH: 22 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="RESIDUE 1 IS PYROGLUTAMIC
        ACID"

(ix) FEATURE:
    (A) NAME/KEY: Modified-site
    (B) LOCATION: 22
    (D) OTHER INFORMATION: /note="RESIDUE 22 IS CYSTEINAMIDE"

(xi) SEQUENCE DESCRIPTION: SEQ ID NO:14:

Xaa Ser Thr Glu Thr Gly Asn Gln His His Tyr Gln Thr Arg Val Val
1               5                   10                  15

Ser Asn Ala Asn Lys Xaa
            20

(2) INFORMATION FOR SEQ ID NO:15:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (ix) FEATURE:

(A) NAME/KEY: Modified-site
(B) LOCATION: 1
(D) OTHER INFORMATION: /note="RESIDUE 1 IS PYROGLUTAMIC ACID"

(ix) FEATURE:
(A) NAME/KEY: Modified-site
(B) LOCATION: 21
(D) OTHER INFORMATION: /note="RESIDUE 21 IS CYSTEINAMIDE"

(xi) SEQUENCE DESCRIPTION: SEQ ID NO:15:

```
Xaa  Lys  Val  Asn  Leu  Lys  Thr  Glu  Glu  Ala  Lys  Pro  Val  Leu  Glu  Asp
 1                    5                        10                       15

Gln  Leu  Ala  Lys  Xaa
                    20
```

(2) INFORMATION FOR SEQ ID NO:16:

(i) SEQUENCE CHARACTERISTICS:
(A) LENGTH: 726 base pairs
(B) TYPE: nucleic acid
(C) STRANDEDNESS: double
(D) TOPOLOGY: unknown (ii) MOLECULE TYPE: cDNA (iv) ANTI-SENSE: NO (ix) FEATURE:
(A) NAME/KEY: misc_signal
(B) LOCATION: 1..54

(ix) FEATURE:
(A) NAME/KEY: CDS
(B) LOCATION: 1..726

(xi) SEQUENCE DESCRIPTION: SEQ ID NO:16:

```
ATG  AAA  AAA  TTG  ATG  ATG  GTT  GCA  CTG  GTC  AGT  TCC  ACT  CTG  GCC  CTT    48
Met  Lys  Lys  Leu  Met  Met  Val  Ala  Leu  Val  Ser  Ser  Thr  Leu  Ala  Leu
 1                    5                        10                       15

TCA  GGG  TGT  GGT  GCG  ATG  AGC  ACA  GCA  ATC  AAG  AAG  CGT  AAC  CTT  GAG    96
Ser  Gly  Cys  Gly  Ala  Met  Ser  Thr  Ala  Ile  Lys  Lys  Arg  Asn  Leu  Glu
                20                        25                       30

GTG  AAG  ACT  CAG  ATG  AGT  GAG  ACC  ATC  TGG  CTT  GAA  CCC  GCC  AGC  GAA   144
Val  Lys  Thr  Gln  Met  Ser  Glu  Thr  Ile  Trp  Leu  Glu  Pro  Ala  Ser  Glu
           35                        40                       45

CGC  ACG  GTA  TTT  CTG  CAG  ATC  AAA  AAC  ACG  TCT  GAT  AAA  GAC  ATG  AGT   192
Arg  Thr  Val  Phe  Leu  Gln  Ile  Lys  Asn  Thr  Ser  Asp  Lys  Asp  Met  Ser
      50                        55                       60

GGG  CTG  CAG  GGC  AAA  ATT  GCT  GAT  GCT  GTG  AAA  GCA  AAA  GGA  TAT  CAG   240
Gly  Leu  Gln  Gly  Lys  Ile  Ala  Asp  Ala  Val  Lys  Ala  Lys  Gly  Tyr  Gln
 65                       70                        75                       80

GTG  GTG  ACT  TCT  CCG  GAT  AAA  GCC  TAC  TAC  TGG  ATT  CAG  GCG  AAT  GTG   288
Val  Val  Thr  Ser  Pro  Asp  Lys  Ala  Tyr  Tyr  Trp  Ile  Gln  Ala  Asn  Val
                85                        90                       95

CTG  AAG  GCC  GAT  AAG  ATG  GAT  CTG  CGG  GAG  TCT  CAG  GGA  TGG  CTG  AAC   336
Leu  Lys  Ala  Asp  Lys  Met  Asp  Leu  Arg  Glu  Ser  Gln  Gly  Trp  Leu  Asn
               100                       105                      110

CGT  GGT  TAT  GAA  GGC  GCA  GCA  GTT  GGT  GCA  GCG  TTA  GGT  GCC  GGT  ATT   384
Arg  Gly  Tyr  Glu  Gly  Ala  Ala  Val  Gly  Ala  Ala  Leu  Gly  Ala  Gly  Ile
          115                       120                      125

ACC  GGC  TAT  AAC  TCA  AAT  TCT  GCC  GGT  GCC  ACA  CTC  GGT  GTA  GGC  CTT   432
Thr  Gly  Tyr  Asn  Ser  Asn  Ser  Ala  Gly  Ala  Thr  Leu  Gly  Val  Gly  Leu
     130                       135                      140

GCT  GCT  GGT  CTG  GTG  GGT  ATG  GCT  GCA  GAT  GCG  ATG  GTG  GAA  GAT  GTG   480
Ala  Ala  Gly  Leu  Val  Gly  Met  Ala  Ala  Asp  Ala  Met  Val  Glu  Asp  Val
145                      150                       155                      160
```

| | | | | | | | | | | | | | | | | |
|---|---|---|---|---|---|---|---|---|---|---|---|---|---|---|---|---|
| AAC | TAT | ACC | ATG | ATC | ACG | GAT | GTA | CAG | ATT | GCA | GAG | CGT | ACT | AAG | GCA | 528 |
| Asn | Tyr | Thr | Met | Ile | Thr | Asp | Val | Gln | Ile | Ala | Glu | Arg | Thr | Lys | Ala | |
| | | | 165 | | | | | 170 | | | | | | 175 | | |
| ACG | GTG | ACA | ACG | GAT | AAT | GTT | GCC | GCC | CTG | CGT | CAG | GGC | ACA | TCA | GGT | 576 |
| Thr | Val | Thr | Thr | Asp | Asn | Val | Ala | Ala | Leu | Arg | Gln | Gly | Thr | Ser | Gly | |
| | | | 180 | | | | | 185 | | | | | | 190 | | |
| GCG | AAA | ATT | CAG | ACC | AGT | ACT | GAA | ACA | GGT | AAC | CAG | CAT | AAA | TAC | CAG | 624 |
| Ala | Lys | Ile | Gln | Thr | Ser | Thr | Glu | Thr | Gly | Asn | Gln | His | Lys | Tyr | Gln | |
| | | 195 | | | | | 200 | | | | | 205 | | | | |
| ACC | CGT | GTG | GTT | TCA | AAT | GCG | AAC | AAG | GTT | AAC | CTG | AAA | TTT | GAA | GAG | 672 |
| Thr | Arg | Val | Val | Ser | Asn | Ala | Asn | Lys | Val | Asn | Leu | Lys | Phe | Glu | Glu | |
| | 210 | | | | | 215 | | | | | 220 | | | | | |
| GCG | AAG | CCT | GTT | CTC | GAA | GAC | CAA | CTG | GCC | AAA | TCA | ATC | GCA | AAT | ATT | 720 |
| Ala | Lys | Pro | Val | Leu | Glu | Asp | Gln | Leu | Ala | Lys | Ser | Ile | Ala | Asn | Ile | |
| 225 | | | | 230 | | | | | 235 | | | | | 240 | | |
| CTC | TGA | | | | | | | | | | | | | | | 726 |
| Leu | | | | | | | | | | | | | | | | |

( 2 ) INFORMATION FOR SEQ ID NO:17:

( i ) SEQUENCE CHARACTERISTICS:
        ( A ) LENGTH: 241 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | |
|---|---|---|---|---|---|---|---|---|---|---|---|---|---|---|
| Met | Lys | Lys | Leu | Met | Met | Val | Ala | Leu | Val | Ser | Ser | Thr | Leu | Ala | Leu |
| 1 | | | | 5 | | | | | 10 | | | | | 15 | |
| Ser | Gly | Cys | Gly | Ala | Met | Ser | Thr | Ala | Ile | Lys | Lys | Arg | Asn | Leu | Glu |
| | | | 20 | | | | | 25 | | | | | 30 | | |
| Val | Lys | Thr | Gln | Met | Ser | Glu | Thr | Ile | Trp | Leu | Glu | Pro | Ala | Ser | Glu |
| | | 35 | | | | | 40 | | | | | 45 | | | |
| Arg | Thr | Val | Phe | Leu | Gln | Ile | Lys | Asn | Thr | Ser | Asp | Lys | Asp | Met | Ser |
| | 50 | | | | | 55 | | | | | 60 | | | | |
| Gly | Leu | Gln | Gly | Lys | Ile | Ala | Asp | Ala | Val | Lys | Ala | Lys | Gly | Tyr | Gln |
| 65 | | | | | 70 | | | | | 75 | | | | | 80 |
| Val | Val | Thr | Ser | Pro | Asp | Lys | Ala | Tyr | Tyr | Trp | Ile | Gln | Ala | Asn | Val |
| | | | | 85 | | | | | 90 | | | | | 95 | |
| Leu | Lys | Ala | Asp | Lys | Met | Asp | Leu | Arg | Glu | Ser | Gln | Gly | Trp | Leu | Asn |
| | | | 100 | | | | | 105 | | | | | 110 | | |
| Arg | Gly | Tyr | Glu | Gly | Ala | Ala | Val | Gly | Ala | Ala | Leu | Gly | Ala | Gly | Ile |
| | | | 115 | | | | | 120 | | | | | 125 | | |
| Thr | Gly | Tyr | Asn | Ser | Asn | Ser | Ala | Gly | Ala | Thr | Leu | Gly | Val | Gly | Leu |
| | 130 | | | | | 135 | | | | | 140 | | | | |
| Ala | Ala | Gly | Leu | Val | Gly | Met | Ala | Ala | Asp | Ala | Met | Val | Glu | Asp | Val |
| 145 | | | | | 150 | | | | | 155 | | | | | 160 |
| Asn | Tyr | Thr | Met | Ile | Thr | Asp | Val | Gln | Ile | Ala | Glu | Arg | Thr | Lys | Ala |
| | | | 165 | | | | | 170 | | | | | | 175 | |
| Thr | Val | Thr | Thr | Asp | Asn | Val | Ala | Ala | Leu | Arg | Gln | Gly | Thr | Ser | Gly |
| | | | 180 | | | | | 185 | | | | | | 190 | |
| Ala | Lys | Ile | Gln | Thr | Ser | Thr | Glu | Thr | Gly | Asn | Gln | His | Lys | Tyr | Gln |
| | | 195 | | | | | 200 | | | | | 205 | | | |
| Thr | Arg | Val | Val | Ser | Asn | Ala | Asn | Lys | Val | Asn | Leu | Lys | Phe | Glu | Glu |
| | 210 | | | | | 215 | | | | | 220 | | | | |
| Ala | Lys | Pro | Val | Leu | Glu | Asp | Gln | Leu | Ala | Lys | Ser | Ile | Ala | Asn | Ile |
| 225 | | | | 230 | | | | | 235 | | | | | 240 | |

Leu (2) INFORMATION FOR SEQ ID NO:18:

(i) SEQUENCE CHARACTERISTICS:
(A) LENGTH: 20 amino acids
(B) TYPE: amino acid
(D) TOPOLOGY: linear (ii) MOLECULE TYPE: peptide (xi) SEQUENCE DESCRIPTION: SEQ ID NO:18:

Asp Pro Arg Val Arg Gly Leu Tyr Phe Pro Ala Gly Gly Ser Ser Ser
1               5                   10                  15

Gly Thr Val Cys
            20

(2) INFORMATION FOR SEQ ID NO:19:

(i) SEQUENCE CHARACTERISTICS:
(A) LENGTH: 21 amino acids
(B) TYPE: amino acid
(D) TOPOLOGY: linear (ii) MOLECULE TYPE: peptide (xi) SEQUENCE DESCRIPTION: SEQ ID NO:19:

Tyr Asp Arg Pro Glu Gly Ile Glu Glu Glu Gly Gly Glu Arg Asp Arg
1               5                   10                  15

Asp Arg Ser Gly Cys
            20

(2) INFORMATION FOR SEQ ID NO:20:

(i) SEQUENCE CHARACTERISTICS:
(A) LENGTH: 25 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="RESIDUE 1 IS ACETYLALANINE"

(ix) FEATURE:
(A) NAME/KEY: Modified-site
(B) LOCATION: 25
(D) OTHER INFORMATION: /note="RESIDUE 25 IS CYSTEINAMIDE"

(xi) SEQUENCE DESCRIPTION: SEQ ID NO:20:

Xaa Thr Asn Phe Val Glu Ser Ile Ile Asn Leu Phe Gln Val Val His
1               5                   10                  15

Asn Ser Tyr Asn Arg Pro Ala Tyr Xaa
            20                  25

(2) INFORMATION FOR SEQ ID NO:21:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1

(D) OTHER INFORMATION: /note="RESIDUE 1 IS
ACETYLTHREONINE"

(ix) FEATURE:
(A) NAME/KEY: Modified-site
(B) LOCATION: 24
(D) OTHER INFORMATION: /note="RESIDUE 24 IS CYSTEINAMIDE"

(xi) SEQUENCE DESCRIPTION: SEQ ID NO:21:

Xaa Glu Pro Asn Leu His Asp Gly Tyr Ala Val Ser Trp Asn Thr Val
1               5                   10                  15

Glu Asp Ser Ile Ile Arg Thr Xaa
            20

(2) INFORMATION FOR SEQ ID NO:22:

(i) SEQUENCE CHARACTERISTICS:
(A) LENGTH: 23 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="RESIDUE 1 IS
ACETYLASPARTATE"

(ix) FEATURE:
(A) NAME/KEY: Modified-site
(B) LOCATION: 23
(D) OTHER INFORMATION: /note="RESIDUE 23 IS CYSTEINAMIDE"

(xi) SEQUENCE DESCRIPTION: SEQ ID NO:22:

Xaa Ser Glu Thr Ala Asp Asn Leu Glu Lys Thr Val Ala Ala Leu Ser
1               5                   10                  15

Ile Leu Pro Gly Ile Gly Xaa
            20

(2) INFORMATION FOR SEQ ID NO:23:

(i) SEQUENCE CHARACTERISTICS:
(A) LENGTH: 39 amino acids
(B) TYPE: amino acid
(D) TOPOLOGY: linear (ii) MOLECULE TYPE: peptide (ix) FEATURE:
(A) NAME/KEY: Modified-site
(B) LOCATION: 39
(D) OTHER INFORMATION: /note="RESIDUE 39 IS CYSTEINAMIDE"

(xi) SEQUENCE DESCRIPTION: SEQ ID NO:23:

Glu Glu Ile Val Ala Gln Ser Ile Ala Leu Ser Ser Leu Met Val Ala
1               5                   10                  15

Gln Ala Ile Pro Leu Val Gly Glu Leu Val Asp Ile Gly Phe Ala Ala
            20                  25                  30

Thr Asn Phe Val Glu Ser Xaa
            35

(2) INFORMATION FOR SEQ ID NO:24:

(i) SEQUENCE CHARACTERISTICS:
(A) LENGTH: 25 amino acids
(B) TYPE: amino acid
(D) TOPOLOGY: linear (ii) MOLECULE TYPE: peptide (x i) SEQUENCE DESCRIPTION: SEQ ID NO:24:

Glu Ser Gln Gly Trp Leu Asn Arg Gly Tyr Glu Gly Ala Ala Val Gly
1               5                       10                      15

Ala Ala Leu Gly Ala Gly Ile Thr Gly
            20              25

(2) INFORMATION FOR SEQ ID NO:25:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (x i) SEQUENCE DESCRIPTION: SEQ ID NO:25:

Ser Thr Glu Thr Gly Asn Gln His Lys Tyr Gln Thr Arg Val Val Ser
1               5                       10                      15

Asn Ala Asn Lys
            20

(2) INFORMATION FOR SEQ ID NO:26:

(i) SEQUENCE CHARACTERISTICS:
      (A) LENGTH: 19 amino acids
      (B) TYPE: amino acid
      (D) TOPOLOGY: linear (ii) MOLECULE TYPE: peptide (x i) SEQUENCE DESCRIPTION: SEQ ID NO:26:

Lys Val Asn Leu Lys Phe Glu Glu Ala Lys Pro Val Leu Glu Asp Gln
1               5                       10                      15

Leu Ala Lys